United States Patent [19]

Comanor et al.

[11] Patent Number: 5,860,917
[45] Date of Patent: Jan. 19, 1999

[54] METHOD AND APPARATUS FOR PREDICTING THERAPEUTIC OUTCOMES

[75] Inventors: Lorraine Comanor, Palo Alto; James M. Minor, Los Altos, both of Calif.

[73] Assignee: Chiron Corporation, Emeryville, Calif.

[21] Appl. No.: 784,206

[22] Filed: Jan. 15, 1997

[51] Int. Cl.$^6$ .......................................................... A61B 5/00
[52] U.S. Cl. ........................... 600/300; 128/923; 128/924
[58] Field of Search ............................ 600/300; 128/923, 128/924, 925

[56] References Cited

U.S. PATENT DOCUMENTS

| | | | |
|---|---|---|---|
| 4,570,225 | 2/1986 | Lundy ...................................... | 364/417 |
| 4,731,725 | 3/1988 | Suto et al. .............................. | 364/415 |
| 4,733,354 | 3/1988 | Potter et al. ............................ | 364/415 |
| 4,839,822 | 6/1989 | Dormond et al. ...................... | 364/513 |
| 5,463,548 | 10/1995 | Asada et al. ........................ | 364/413.02 |
| 5,517,405 | 5/1996 | McAndrew et al. .................... | 364/401 |
| 5,619,990 | 4/1997 | Kanai ..................................... | 128/630 |
| 5,642,731 | 7/1997 | Kehr ....................................... | 128/630 |
| 5,642,936 | 7/1997 | Evans ..................................... | 128/630 |
| 5,687,716 | 11/1997 | Kaufmann et al. .................... | 128/630 |

OTHER PUBLICATIONS

Chui, et al., *Use of neural networks to analyze drug combination interactions*, 1993, American Statistical Association, 1993 Proceedings of the Biopharmaceutical Section.

Minor, James. M., *Neural networks for drug interaction analysis*, 1993, American Statistical Association, 1993, Proceedings of the Biopharmaceutical Section.

Namini, et al, *Application of neural networks to analyze clinical trail data*, 1993, American Statistical Association, 1993 Proceedings of the Biopharmaceutical Section.

Watson, et al., *Analysis of the stability properties of a drug formulation through the use of neural networks.*, 1993, American Statistical Association, 1993 Proceedings of the Biopharmaceutical Section.

Minor et al. *From here to there (Dosing to Efficacy) with neural nets.*, 1994, American Statistical Association, 1994 Proceedings of the Biopharmaceutical Section.

Minor, J.M., *Data Analysis with Ffanns,* 1989, Proceedings of the ISA/89 International Conference and Exhibit Philadelphia, Pennsylvania, Advances in Instrumentation and Control, vol. 44, Part 3., pp. 1155–1168.

Minor, J.M., *SMILES and FFANNS: Similarity Least Squares and Feed Forward Artificial Neural Networks,* 1989, IJCNN International Joint Conference of Neural Networks, Washington, D.C.

(List continued on next page.)

*Primary Examiner*—Marvin M. Lateef
*Assistant Examiner*—Eleni Mantis Mercader
*Attorney, Agent, or Firm*—Beyer & Weaver; Sharon M. Fujita; Robert P. Blackburn

[57] ABSTRACT

Methods, software, and systems for evaluating the response of a patient afflicted with a disease to a therapeutic regimen for the disease are described. In one aspect, the present methods, systems, and software are provided for evaluating the utility of a treatment regimen for treating a patient afflicted with a disease. In one embodiment of this aspect, the value of at least one diagnostic variable relating to a statistical model describing the utility of the treatment regimen is determined. The statistical model is derived using a robustified similarity metric least squares (SMILES) analysis of the response to the treatment regimen which has been adapted to include discriminant and logistical analysis. The value of the diagnostic variable is then applied to the model to provide an estimated utility of the treatment regimen in treating the patient. Using the methods, software, and apparatus described herein, robust, statistically significant models of patient responsiveness that reduce the problems associated with present treatment response prediction methods that are brittle and oversimplify the complex interactions among treatment variables can assist patients and clinicians in determining therapies.

68 Claims, 7 Drawing Sheets

OTHER PUBLICATIONS

Minor, J.M., *Introduction Neural Networks,* Oct. 14–18, 1990, published in Advances in Instrumentation and Control, vol. 45, Proceedings of ISA90 International Conference and Exhibit.

Minor, et al., *Smiles, Parity, and Feature Recognition,* 1990, IJCNN–90–WASH D.C. vol. II Applications Track. Jan. 15–19, 1990.

Miller, et al., *A Two–Dimensional Model of Stratospheric Chemistry and Transport,* Dec. 20, 1981, Journal of Geophysical Research, vol. 86, No. C12, pp. 12039–12065.

Minor, J.M., *Applied Neural Nets Industrial Strength Solutions,* (Sep. 30–Oct. 2, 1991). Proceedings of the 17th Annual Advanced Control Conference.

Minor et al., *Neural Net Methods for Mapping Thermodynamic and Physical Properties in Environment Problems,* paper in 1996 AIChE Spring National Meeting, New Orleans, LA. Feb. 25–29, 1996.

Knodell, et al., *Formulation and Application of a Numerical Scoring System for Assessing Histological Activity in Asymptomatic Chronic Active Hepatitis,* 1981, Hepatology, vol. 1. No. 3. p. 431.

Minor et al., *Generalized Ridge Analysis with Application to Population Pharmacokinetics/Dynamics,* 1996. Journal of Biopharmaceutical Statistics, 6(1), 105–114.

Minor, et al., *Analysis of clinical data using neural nets.,* 1996. Journal of Biopharmaceutical Statistics, 6(1), 83–104.

Minor, J.M., Watson, G.A., *Competitive Advantage via Advanced Technology: Neural Networks and Quality Control,* Apr. 1995, Proceedings QC 95.

Minor, et al. *Use of Neural Networks to Analyze Drug Combination Interactions,* Proceedings ComCon4, Rodos Palace Hotel, Rhodes, Greece 14–18 Jun. 1993.

Bisceglie, et al., *A Randomized, Controlled Trial Of Recombinant α–Interferon Therapy for Chronic Hepatitis B,* 1993, The American Journal of Gastoenterology, vol. 88. No. 11, pp. 1887–1892.

James E. Minor, *Data Analysis with Neural Nets And Strategy of Research,* May, 1990, Accession No. 17526, E.I. du Pont de Nemours and Company.

James E. Minor, *Practical Neural Nets,* Feb. 1990, Accession No. 17503. E.I. du Pont de Nemours and Company.

Lau et al., Mini Poster entitled "Statistical Models for Predicting a Beneficial Response to ALPHA Interference In Patients with Chronic Hepatitis B", Presented at American Association for the Study of Liver Disease (AASLD), Nov. 1996.

Lau et al., Abstract entitled "Statistical Models for Predicting a Beneficial Response to ALPHA Interference In Patients with Chronic Hepatitis B", AASLD Abstracts, Oct. 1996.

Summers et al., "Casual Probabilistic Modelling for Clinical Decision Support in the High Dependency Environment" *Proceedings of the Annual International Conference of the IEEE Engineering in Medicine and Biology Society* Oct. 29, 1992.

METHOD AND APPARATUS FOR PREDICTING THERAPEUTIC OUTCOMES

BACKGROUND OF THE INVENTION

1. The Field of the Invention

The present invention relates to software, methods, and devices for evaluating correlations between observed phenomena and one or more factors having putative statistical relationships with such observed phenomena. More particularly, the software, methods, and devices described herein relate to the prediction of likely therapeutic outcomes for patients being treated with a therapeutic regimen.

2. Background

The application of statistical methods to the treatment of disease has been one of the great success stories of modem medicine. Using statistical methodologies, physicians and scientists have been able to identify sources, behaviors, and treatments for a wide variety of illnesses that have haunted humankind for centuries. Thus, for example, in the developed world, diseases such as cholera have been eradicated due in great part to the understanding of the causes of, and treatments for, these diseases using statistical analysis of the various risk and treatment factors associated with these diseases.

One particularly important application of statistical methods to medicine is the evaluation of the efficacy of regimens for treating diseases, and the use of statistical models to determine the likelihood of a particular patient's response to a treatment regimen. The latter application is especially important as treatment regimens for many diseases such as cancer, heart disease, and viral infections, including hepatitis B ("HBV"), hepatitis C ("HCV"), and acquired immune deficiency syndrome ("AIDS"), require a great deal of sacrifice on the part of the patient undergoing treatment in terms of cost, changes in lifestyle, and/or physical discomfort, with potentially problematic results. For example, therapy options for HBV are mostly limited to a course of interferon-$\alpha$ ("IFN$\alpha$") treatments which have unpleasant side effects and are expensive. Indeed, some patients undergoing IFN$\alpha$ treatments for HBV are so burdened by the side effects of treatment they opt out of therapy entirely, even when the treatment is showing efficacy. In addition, only about one-third of those afflicted with HBV have a positive response to IFN$\alpha$ treatment (DiBisceglie, Fong et al. 1993). Even where the side effects of a treatment regimen are not so profound, statistical methods can be used to assist the physician and patient in evaluating treatment options. Thus, it is of great benefit for clinicians to have access to methods for evaluating the likelihood of the success of a treatment regimen before prescribing that regimen to a patient afflicted with a given disease.

In particular, HBV is a difficult disease to model. This difficulty is due at least in part to the highly complex nature of the interaction between HBV pathogen and its host. Aspects of this complex interaction include the variation of HBV levels in the host's blood stream during certain phases of the host's life cycle, the influence of the host's sex on HBV, the influence of the host's environment on HBV, and the interactions among HBV and other viruses that may infect the host such as AIDS or malaria (Coveney and Highfield; Blumberg 1994). Thus, any model for the prediction of therapeutic outcomes for HBV treatment will have to account for a variety of highly complex interactions within the virus-host system.

In general, the statistical methods used in medical applications have been limited to so-called logistic regression methods that relate clinical variables gathered from patients being treated for a disease with the probable treatment outcomes for those patients. Logistic regression methods are used to estimate the probability of defined outcomes as impacted by associated information. Typically, these methods utilize a sigmoidal logistic probability function (Dillon and Goldstein 1984) that is used to model the treatment outcome. The values of the model's parameters are determined using maximum likelihood estimation methods. The non-linearity of the logistic probability function, coupled with the use of the maximum likelihood estimation procedure, makes logistic regression methods complicated. Thus, such methods are often ineffective for complex models in which interactions among the various clinical variables being studied are present. In addition, the coupling of logistic and maximum likelihood methods limits the validation of logistic models to retrospective predictions which can overestimate the model's true abilities.

Logistic models can be combined with discriminant analysis to consider the interactions among the clinical variables being studied to provide a linear statistical model that is effective to discriminate among patient categories (e.g., responder and non-responder). Often these models comprise multivariate products of the clinical data being studied and utilize modifications of the methods commonly used in the purely logistic models. In addition, the combined logistic/discriminant models can be validated using prospective statistical methods in addition to retrospective statistical methods to provide a more accurate assessment of the model's predictive capability. However, these combined models are effective only for limited degrees of interactions among clinical variables and thus are inadequate for many applications.

Furthermore, both purely logistic and combined logistic/discriminant regression models are designed to correlate clinical variables, or products of clinical variables, with estimates of likely treatment outcome. Although the relationship between the clinical variables for a patient and the likely treatment outcome for that patient has utility, it will be appreciated that a clinician is more concerned with a patient than a set of clinical test results. Thus, the very basis on which traditional logistic regression commonly used in predicting therapeutic outcomes has to be questioned.

What is needed, therefore, are methods of providing statistically meaningful models for predicting likely treatment outcomes for specific treatment regimen that model the complex interactions among patient variables in a statistically robust manner. Moreover, there is a need for providing methods and systems that assist clinicians and patients in choosing a treatment regimen by providing both clinician and patient with a statistically meaningful estimation of the probability of a successful treatment outcome under the regimen being considered.

SUMMARY OF THE INVENTION

The present invention provides methods, software, and systems for evaluating the response of a patient afflicted with a disease to a therapeutic regimen for the disease. Using the methods, software, and apparatus described herein, robust, statistically significant models of patient responsiveness to treatment regimens can be developed and utilized to assist patients and clinicians in determining treatment options. Thus, the present invention will be seen to reduce the problems associated with present treatment response prediction methods that are brittle and oversimplify the complex interactions among treatment variables.

In one aspect, the present invention provides methods, systems, and software for evaluating the utility of a treatment regimen for treating a patient afflicted with a disease. In one embodiment of the method of the invention, the value of at least one diagnostic variable relating to a statistical model describing the utility of the treatment regimen is determined. The statistical model is derived using a discriminant function which is effective for classifying the response of an individual afflicted with the disease to the treatment regimen in question. This discriminant function is based at least in part on the diagnostic variable and a data set of patients who have been treated with the regimen in question. A logistic regression using the discriminant function is then performed to assign a probability of treatment outcome for the individuals being treated using the treatment regimen. The value of the diagnostic variable is then applied to the model to provide an estimated utility of the treatment regimen in treating the patient.

According to one embodiment of this aspect of the present invention, the estimate includes a projected likely treatment outcome score. According to another embodiment, the discriminant function can include a polynomial function. In still another embodiment, the discriminant function is developed using a similarity-metric least squares (SMILES) analysis of the data set. Particular diseases having treatment regimen that can by analyzed using this aspect of the invention include HBV, HCV, and AIDS.

In another aspect, the present invention provides methods, systems, and software for producing a statistical model of the likely response to a treatment regimen for treating a disease in a mammal. In one embodiment of the method of the invention, at least one sample population of individuals representative of the disease, and being treated with the treatment regimen under study, is obtained. At least one variable having a putative relationship with the disease is determined that relates to the population, the disease, or the treatment regimen. From this data a model of the likely response to the treatment regimen is derived. The steps of derivation include standardizing the data; processing the data using the above-described method; robustifying the preliminary model; and analyzing the results of the model using a logistic analysis to provide a statistical model of the response to the treatment regimen.

In one embodiment, the step of standardizing the data includes calculating the mean and standard deviation for the data, subtracting the mean from each data point, and dividing that difference by the standard deviation. In another embodiment of this aspect of the invention, null data is used to augment the original data. In still another embodiment, the SMILES analysis used to derive the discriminant function from the data set includes defining a set of patient vectors from which set a set of nodes is derived. The distance between the patient vectors and nodes is determined from which distance a set of similarity values is derived. The similarity values are subjected to a regression analysis from which a set of predicted outcome values is derived. These predicted outcome values are regressed on to provide a set of weighting coefficients and robustifying the model. This is performed, in some embodiments, using a Ridge regression.

In some embodiments, the similarity values are defined using a monotonic, decreasing function. This function can be chosen from the group of functions including:

$$\frac{1}{D_{ij} + \epsilon} \beta e^{-\alpha D_{ij} + \gamma},$$

and $$\frac{1}{1 + \gamma e^{\alpha D_{ij} + \beta}}$$

where $D_{ij}$ is the difference between the $i^{th}$ patient vector and the $j^{th}$ node, and $\alpha$, $\beta$, $\gamma$, and $\delta$ are suitable coefficients. In one particular embodiment, $\alpha$ is chosen such that the square of the standard deviation of said data is about 1.5s, where s is the number of variables in said statistical model.

In still another aspect, the present invention provides methods, software, and systems for optimizing testing schedules for determining the efficacy of a regimen for treating a disease in a mammal. In one embodiment, the method includes evaluating a statistical model describing the treatment regimen for at least two time periods. The statistical model is derived using the above-described method to determine thereby the optimal testing schedule for predicting the efficacy of the method.

These and other aspects and advantages of the present invention will become more apparent when the Description below is read in conjunction with the accompanying Drawings.

BRIEF DESCRIPTION OF THE DRAWINGS

FIG. 7A represents the results for a treatment model at month 0 of treatment. FIG. 7B represents the results for a treatment model at month 1 of treatment.

DESCRIPTION OF SPECIFIC EMBODIMENTS

The present invention provides methods, apparatus, and software for evaluating the likelihood of a patient's responsiveness to a treatment regimen for treating a disease. Using the methods, apparatus, and software as exemplified herein, patient responsiveness can be evaluated before or during the application of a treatment regimen for a disease that afflicts the patient being treated to provide thereby critical information to the patient and clinician as to the risks, burdens, and benefits associated with a particular treatment regimen. It will be appreciated, therefore, that the methods, apparatus, and software exemplified herein can serve to improve a patient's quality of life and odds of treatment success by allowing both patient and clinician a more accurate assessment of the patient's treatment options.

In a first aspect, the present invention provides a method for producing a statistical model of the likely response of a patient to a treatment regimen for treating a disease in a mammal. As used herein "treatment regimen" is defined to be a therapeutic protocol for curing or reducing the symptoms associated with a disease state in a patient. Typically the patient is a human, but it will be appreciated that the patient can be any mammal such as, but not limited to, dogs, cats, cows, sheep, horses, pigs, or the like. The disease being treated will be understood to be any ailment for which a treatment regimen can be defined. Examples of diseases include, but are not limited to, cancer, viral infections, fungal infections, bacterial infections, chronic pain, and degenerative illnesses. In one embodiment, the methods of the present invention are applied to modelling patient responsiveness to treatments for hepatitis B virus ("HBV"), hepatitis C virus ("HCV") and acquired immune deficiency syndrome ("AIDS"). In addition, the methods described herein can be used in conjunction with prediction the response of any complex system such as a living organism, either plant (e.g., crops), non-mammal, or mammal, to a treatment regimen or other course of applied stimulus.

Figure 1:
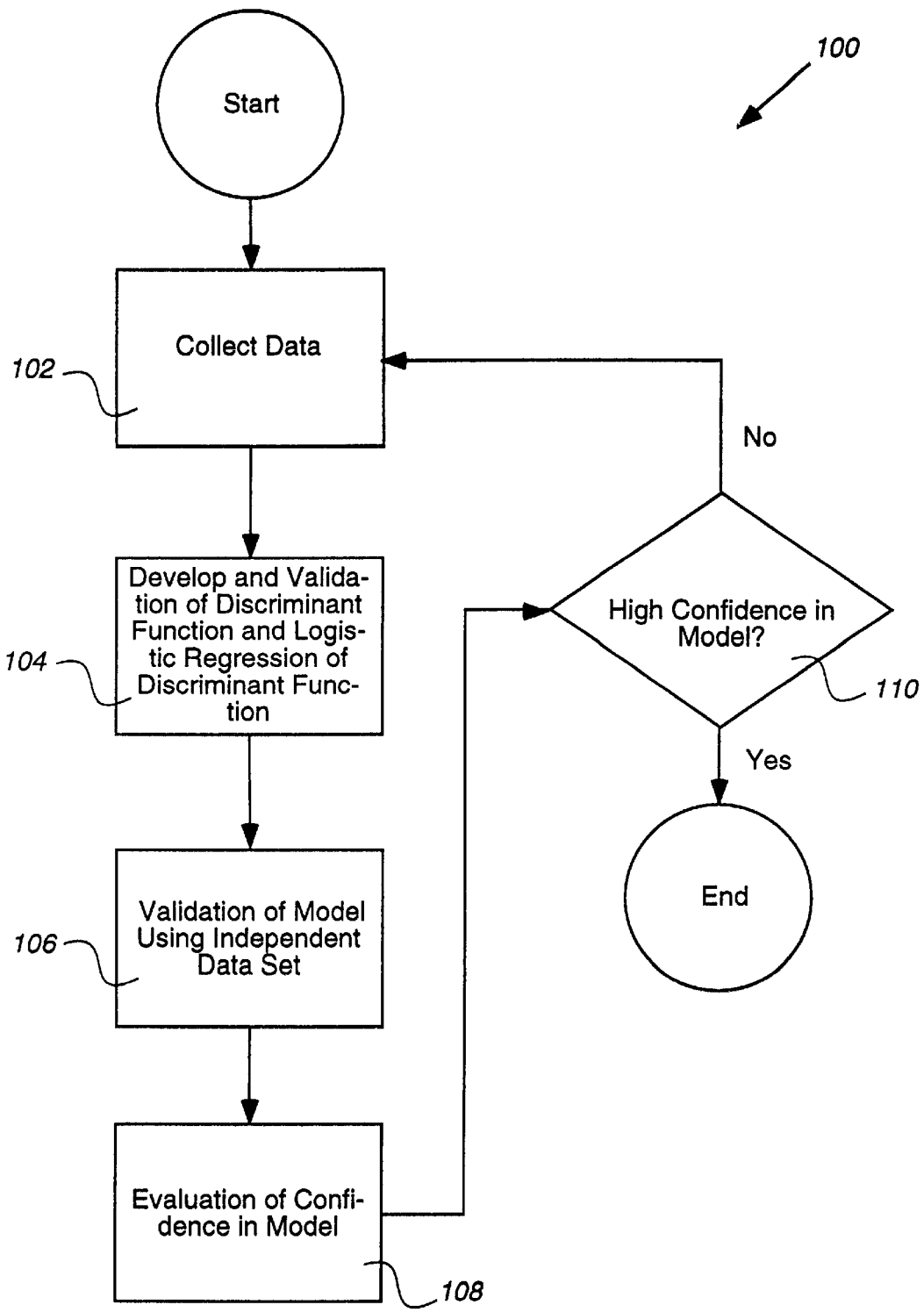
FIG. 1 is a flow chart illustrating a method for creating a statistical model to predict the likely outcome of a therapeutic regimen on a patient in accordance with the present invention.

Referring to FIG. 1, which illustrates one embodiment of a method in accordance with this first aspect of the invention at 100, the development of a statistical model for predicting the responsiveness of a patient to a treatment regimen for a disease begins with the collection of clinical data at step 102. This may include the use of various experimental design strategies, such as factorial analysis. As used herein, "clinical data" (also referred to herein as "clinical variables") can be any information that has utility in developing a predictive model of patient responsiveness. This data can be gathered from direct examination of one or more patients or individuals, or it may be obtained from existing databases. The data will be gathered from a population of individuals (the "sample population") that is sufficient to produce a statistically significant model. The size of the sample population will depend on the details of the predictive model being developed and can be determined using methods known to those of skill in the statistics and medical arts.

Typically, though not always, the data gathered in step 102 will have some biochemical, biophysical, genetic, or other mechanistic relationship with the etiology or manifestation of the disease being treated. Thus, it will be appreciated that the actual choice of data to be gathered will depend on the disease being treated as will be familiar to those of skill in the medical arts. In addition, the data gathered can comprise values that are continuous or quasi-continuous (e.g., enzyme concentration), digitized data (e.g., electrocardiogram traces or magnetic resonance images), or can comprise discrete data such as gender, or values derived using a reference scale (e.g., degree of pain). Examples of data gathered in step 102 include, but are not limited to, age, gender, blood counts (e.g., white or red blood cell counts or hematocrits), antibody or antigen presence and/or concentrations, enzyme concentrations, presence or absence of antigenic determinants (e.g., the presence or absence of CD4 with respect to acquired immune deficiency syndrome), degree of disease progression (e.g., disease stage), presence or absence of cachexia (wasting), dosage of drug(s) being given to the patient, degree of pain, presence or absence of genetic markers, the presence or absence of genetic mutations (in the patient or infectious organism(s)), family history of disease, and the presence or absence of physical manifestations of the disease and the degree of any such manifestation (e.g., degree of fibrosis). As noted above, the choice of clinical variables to be examined will depend on the disease being treated and will be familiar to those of skill in the medical arts, as will the materials and methods required to obtain such data.

Once the data has been collected, a "discriminant function" is constructed at step 104 using the data obtained at step 102, and which step will be discussed in greater detail below with respect to FIG. 2. As used herein, the term "discriminant function" refers to a mathematical function or construct that is determined to be statistically effective to classify individuals into mutually exclusive and exhaustive groups on the basis of a set of independent variables (Dillon and Goldstein 1984), and will be discussed in greater detail below. The set of independent variables will typically comprise the data gathered in step 102. Following the development and initial validation of the robustified discriminant function, the discriminant function is further validated in step 106 by applying the model to a second sample population that is independent of the sample population used to develop the discriminant function. The model is then evaluated in step 108 to assess its predictive performance. If it is determined there is high confidence in the model in step 110, then the process terminates. Otherwise, the process moves back to step 102 where additional data is collected and a new discriminant is developed. The determination of the model's performance can be accomplished using methods known to those skilled in the statistics arts.

Figure 2:
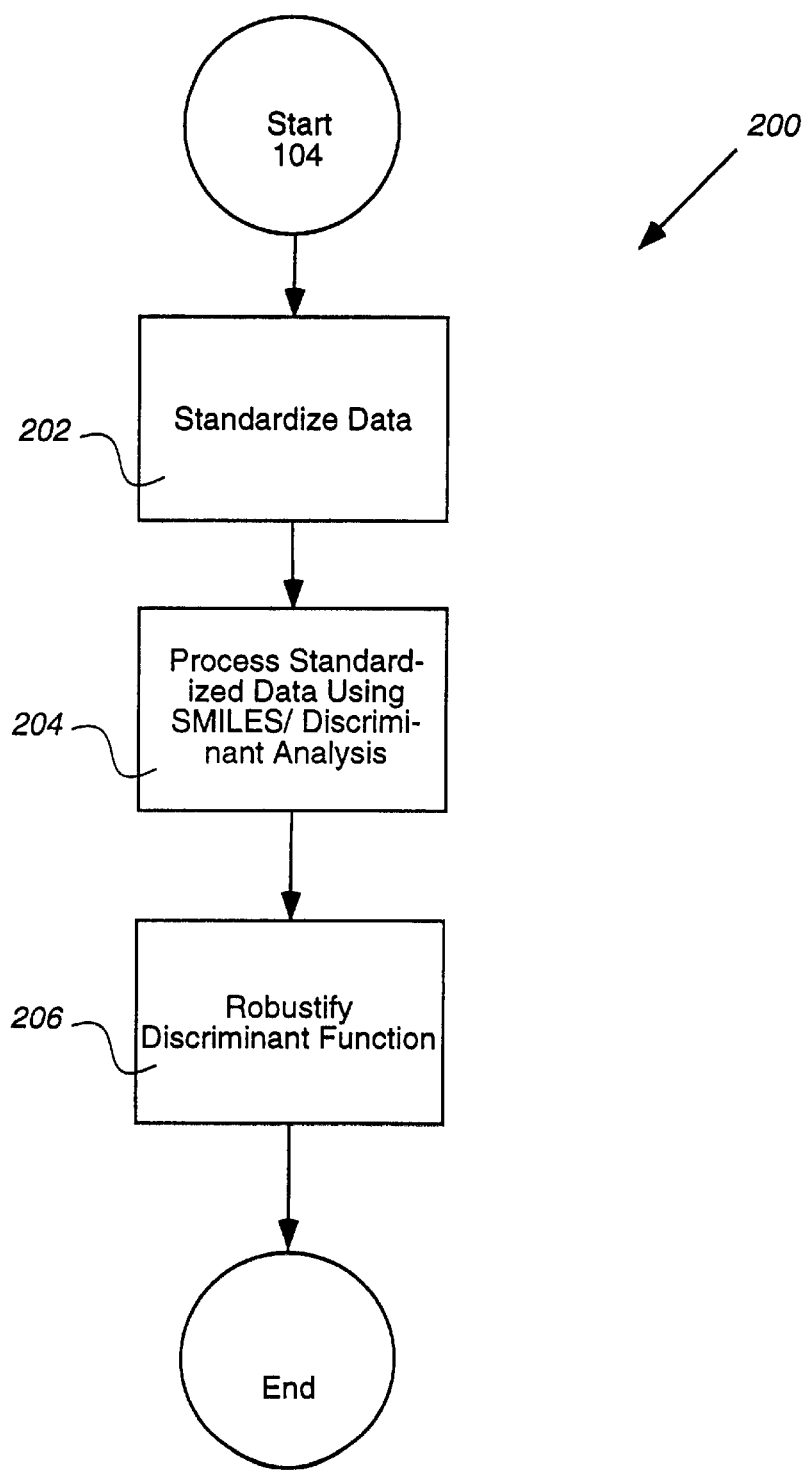
FIG. 2 is a flow chart illustrating step 104 of FIG. 1 in greater detail.
Figure 3:
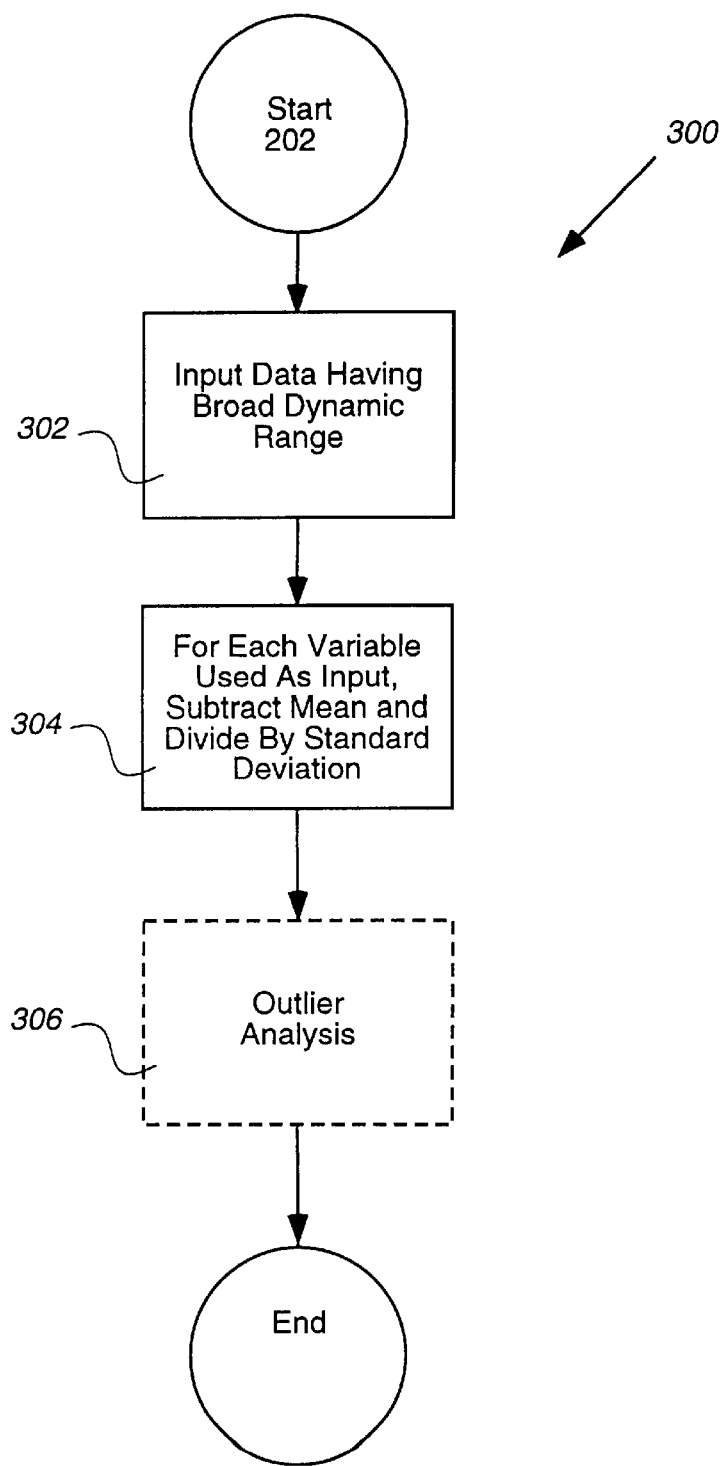
FIG. 3 is a flow chart illustrating step 202 of FIG. 2 in greater detail.

FIG. 2 at 200 illustrates the steps associated with the development of a discriminant function (step 104 of FIG. 1) in accordance with one embodiment of the invention. Beginning at step 202, the data collected in step 102 is standardized so that variables representing different physical quantities can be compared. The process of standardization allows for the evaluation of data having a broad dynamic range; thereby facilitating the data analysis. One method of performing the standardization of step 202 is shown in FIG. 3 at 300, in which data having a broad dynamic range is input at step 302. At step 304 the average and standard deviation for each set of variables is determined and a set of standardized variables is calculated by first subtracting the average value for a particular variable from each value of the set of values for that variable. The difference is then divided by the standard deviation for the set of values for that variable. An optional outlier and/or residual analysis can be performed at step 306 to evaluate the results of the regression analysis. These analyses can include, but are not limited to: the ranking of variables and effects; step-wise simplification of the model to achieve parsimony; outlier processing; and/or the analysis of residual patterns. An example of this procedure is also provided in the Example below.

Referring back to FIG. 2, the standardized data is then processed at step 204 using discriminant analysis to obtain a discriminant function to predict the likely treatment response of a patient to the treatment regimen being studied. The discriminant function used can be any function effective for discriminating between the various outcomes of the treatment regimen. Usually the possible outcomes will be responder or non-responder, although more than two outcomes can be handled as well. In one embodiment, the discriminant function includes a polynomial function. Such function are generally useful for systems in which the influence of interactions among the variables of the statistical model beyond pairwise interactions is minimal. Polynomial functions are also generally more efficient in terms of computational complexity. Thus, polynomial discriminant functions will be recognized as being useful for models having a moderate degree of complexity. However, in some cases polynomial discriminant functions can be used to derive models in which the interactions among the variables are more complex, e.g., where the predictive results of the model so produced are used for determining outcomes where the effects of interactions among the variables beyond pairwise interactions have little relative influence on the model's predictive ability. Still other classes of functions useful for deriving the discriminant function will be apparent to those of skill in the statistics arts.

In another embodiment, the discriminant function is derived using similarity-metric least squares ("SMILES") analysis. The SMILES analysis is premised on the assumption that entities having similar profiles also will have similar responses to the regimen being modeled. In the context of the present invention, the "entities" are the patients being treated and the "profiles" are the clinical profiles of the patients as defined by the clinical data gathered in step 102. Rather than performing regression analysis directly on the clinical information of individual patients, the SMILES analysis includes regression analysis on the similarities between patients' clinical information. To do this, the SMILES model uses object-oriented regression in which the clinical information and response of each patient is treated as an single mathematical object. Objects (patients or subjects included in the model) that are mathematically similar will have a high probability of having the same or very similar responses to treatment. Conversely, objects that are not similar will have a low probability of having the same or similar response to treatment. By design, the SMILES model requires objects to work together to produce a consistent pattern of prediction. Hence, the effects of noise, i.e., spurious or erroneous clinical information, tend to be filtered out. This reduces the impact of atypical patient profiles (outliers) on the performance of the model. In addition, such an approach will be recognized as being more compatable with clinical medical practice by emphazing the similarities and differences among patients as opposed to the prediction of various clinical quantities.

Figure 4:
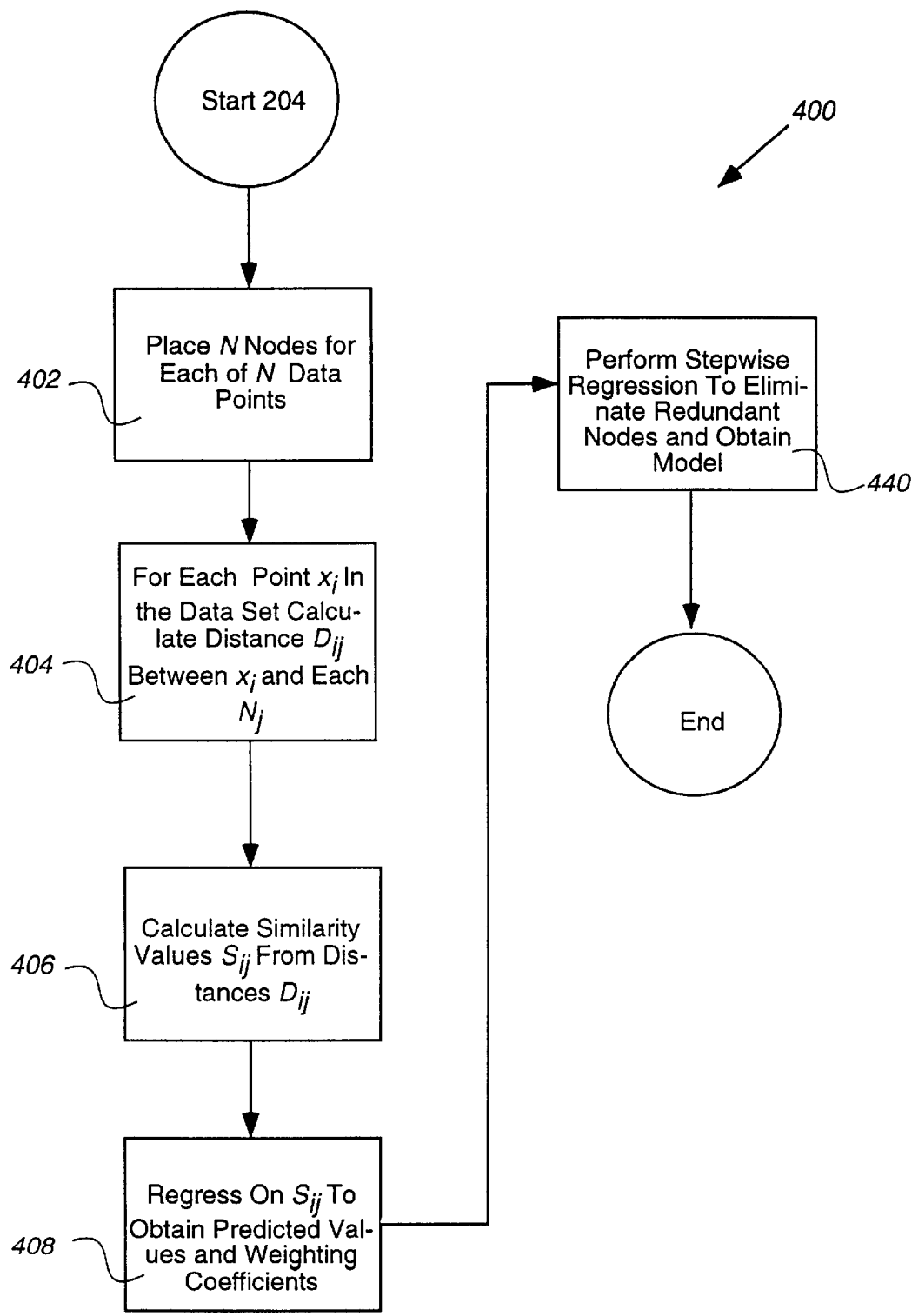
FIG. 4 is flow chart illustrating step 204 of FIG. 2 in greater detail.

In one embodiment of step 204, illustrated in FIG. 4 at 400, vector analysis is used as a method for organizing the multivariate information of each patient's clinical profile. Beginning at step 402 a vector $\vec{P}_i$ is created for each patient in the model. Each element of the vector is the value of a specific clinical variable determined for that patient in step 102, i.e., $$\vec{P}_i = \begin{pmatrix} \overline{P}_1 \\ \cdot \\ \cdot \\ \cdot \\ \overline{P}_n \end{pmatrix}$$

where $\overline{P}_m$ is the $m^{th}$ clinical variable for the $i^{th}$ patient (e.g., CD4 count, liver enzyme concentration, gender indicator, or Knodell liver biopsy score) and n is the number of clinical variables being used to describe the patient.

In one embodiment, a set of nodes $\vec{N}_j$ that will be used to construct the model is defined by the determination of a parsimonious subset of unique patient vectors $\vec{P}_i$ using conventional statistical methodologies:

$$\vec{N}_j = \begin{pmatrix} \overline{N}_1 \\ \cdot \\ \cdot \\ \cdot \\ \overline{N}_n \end{pmatrix}$$

In one embodiment, step-wise regression on the set of patient vectors $\vec{P}_i$ is performed to obtain the parsimonious set of nodes $\vec{N}_j$. As used herein, the term "unique" refers to entities that are not substantially statistically indistinguishable, i.e., so close in character that they cannot be considered statistically different. It will be appreciated that the set of nodes $\vec{N}_j$ represents a minimal "basis set" of vectors from which the model can be constructed.

In another embodiment, a second set of "null" patient vectors having identical profiles, but indeterminate outcome prediction values (i.e., 50% chance of response/non-response) is constructed and added to the set of patient vectors $\vec{P}_i$. Without wishing to be bound to any particular theory, it has been found that such an augmentation provides greater model stability during the prospective prediction process which is described below by reducing the chance of "optimistic" and outlier results. In addition, such augmentation minimizes undesirable residual effects of the set of basis functions that are derived from the set of nodes as described below. The use of a set of "phantom patient vectors" has no effect on the final predictions of likely treatment outcome as the vectors are "information neutral" as such vectors describe a truly indeterminate outcome.

Figure 5:
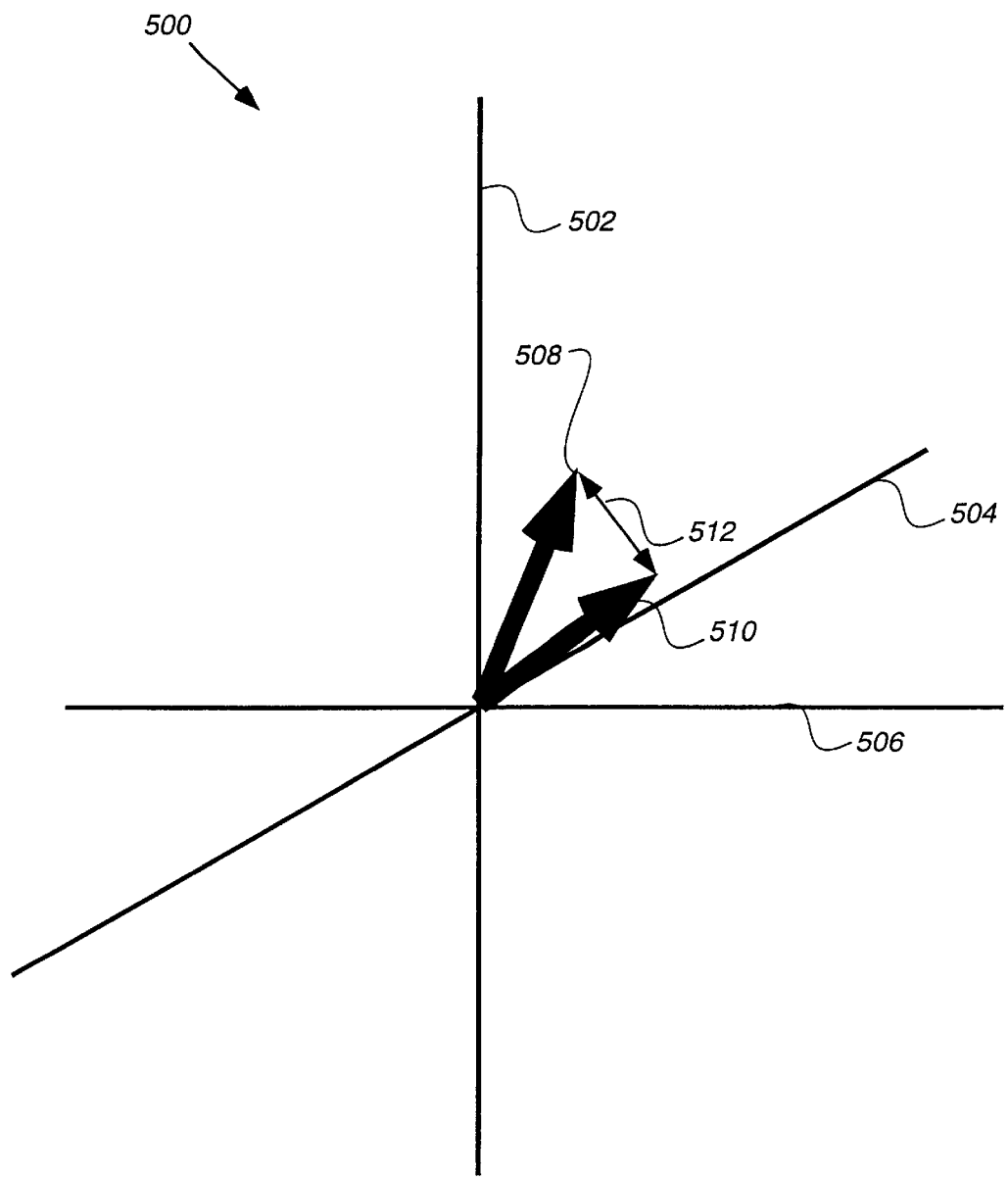
FIG. 5 is an illustration of a "patient vector" and a "node" constructed in accordance with the present invention.

At step 404 a distance $\vec{D}_{ij} = \vec{P}_i - \vec{N}_j$ is calculated between each unique patient vector and each node. The square of the magnitude of this distance $D_{ij}^2$ is given by the relation (1):

$$D_{ij}^2 = \vec{D}_{ij} \cdot \vec{D}_{ij} = \sum_{k=1}^{S} (\overline{P}_{ik} - \overline{N}_{kj})^2. \tag{1}$$

where s is the number of clinical variables, and $\overline{P}_{ik}$ and $\overline{N}_{kj}$ (k=1, ..., s) represent the clinical variable for the $i^{th}$ and $j^{th}$ patient and node respectively. This distance is illustrated in FIG. 5 at 500, wherein a co-ordinate system comprising axes 502, 504, and 506 is used to define a patient vector 508 and a node 510. The distance $D_{ij}^2$ is represented by square of the magnitude of the two-headed arrow 512. When $\vec{P}_i$ and $\vec{N}_j$ are close, the magnitude squared of the vector difference (1) is small. Conversely, when $\vec{P}_i$ and $\vec{N}_j$ are far apart, the magnitude squared of the vector difference is large. Hence, the more similar the clinical profile of patient i is to the clinical profile of patient j, the smaller the magnitude squared of the vector difference, and the greater the likelihood that these two patients will have the same or a similar response to treatment.

With continued reference to FIG. 4, in step 406 similarity scores $S_{ij}$ are calculated from the vector distances determined in step 404, which similarity scores comprise localized basis functions from which the statistical model is constructed. It will be appreciated that the distance $D_{ij}^2$ determined in equation (1) is actually a measure of dissimilarity between $\vec{P}_i$ and $\vec{N}_j$. As will be appreciated, a reciprocal relationship exists between dissimilarity and similarity. In one embodiment, $S_{ij}$ is a monotonic, decreasing function of the distance $D_{ij}$. Examples of suitable monotonic, decreasing functions include, but are not limited to:

$$\frac{1}{D_{ij}+\epsilon}\beta e^{-\alpha D_{ij}+\gamma},$$

and $$\frac{1}{1+\gamma e^{\alpha D_{ij}+\beta}}$$

where $\alpha$, $\beta$, $\gamma$, and $\epsilon$ are coefficients, with $\alpha$ and $\epsilon$ both greater than zero. Still other suitable functions will be apparent to those of skill in the statistics arts. It will be appreciated that the last similarity function, $(1+\gamma e^{\alpha D_{ij}+\beta})^{-1}$, can be obtained using a variant of the above-described patient vector $\vec{P}_i$, $\vec{P}'_i$, that includes the square of the magnitude of $\vec{P}_i$ as an element, i.e., $$\vec{P}'_i = \begin{pmatrix} \vec{P}_1 \\ \cdot \\ \cdot \\ \cdot \\ \vec{P}_n \\ \|\vec{P}_i\|^2 \end{pmatrix},$$

in combination with a neural network (Minor and Namini 1996).

In one embodiment of the present invention, the dissimilarity determined in equation (1) is transformed into a similarity score using the following equation:

$$S_{ij} = \frac{1}{e^{D_{ij}^2/\sigma^2}} \tag{2}$$

where $\sigma$ is a statistical parameter that controls the degree of overlap among the localized basis functions, thereby controlling the non-orthogonality of the basis functions. In one embodiment of the present invention, $\sigma$ is about 1.5 times the number of clinical variables considered in the model, i.e., $\sigma \approx 1.5s$. In some cases, $\sigma$ can vary not only between patients, but between clinical variables (i.e., $\sigma$ can be treated as a vector). In those cases where the available data is "dense" or quasi-continuous, such as in an EKG trace or in a field such as an MR image, $\sigma$ can also be a function of spatial location.

In general, the value for $\sigma$ should be chosen to provide strong correlation (overlap) among the localized basis functions, although care should be taken to avoid overly strong correlations as this can result in predicted outcome probabilities that are constant for all patients. However, too little correlation will tend to produce a mode which overfits the data and includes useless, statistically meaningless noise. Without wishing to be bound to any particular theory of operation, it has been found that the use of non-orthogonal localized basis functions as described by present invention is highly effective at discerning patterns of statistically significant information from the clutter of background statistical noise inherent in statistical modelling. The approach of using non-orthogonal functions will be recognized as unique in the statistics arts in which orthogonal basis functions are almost universally used for creating statistical models.

In step 408 a regression analysis of the similarity scores is performed to obtain predicted treatment outcome scores and coefficients that weight the nodes used to construct the model. In one embodiment, a linear regression analysis (Kshirsager 1972) is performed to provide an optimized estimate of the discriminant function for the $j^{th}$ patient $\Delta_j$ using equation (3):

$$\Delta_j = I_1 + \sum_{i=1}^{r} w_i S_{ij} \tag{3}$$

where $w_i$ are weighting coefficients, r is the number of nodes $\vec{N}_j$, and $I_1$ is the intercept. Using the expression for $S_{ij}$ in equation (2) yields:

$$\Delta_j = I_1 + \sum_{i=1}^{r} w_i e^{-D_{ij}^2/\sigma^2}. \tag{4}$$

In one embodiment, the regression to determine the weights $w_i$ is performed using techniques that retain non-orthogonality among the nodes using so-called Ridge regression techniques (Huber 1981; Minor 1996). Such regressions can be performed using commercially available statistical analysis software. At step 410, a second regression is performed to eliminate redundant nodes and thereby obtain a parsimonious model which has the same form as shown in equations (3) and (4), but which uses a minimal number of nodes. In one embodiment, Ridge regression techniques are employed for the stepwise regression.

Returning to FIG. 2, upon completion of the SMILES/discriminant analysis the model produced is "robustified" at step 206. As used herein, the term "robustified" refers to additional processing to a given treatment model so that the model is reasonably statistically insensitive to small deviations from the assumptions underlying the model (Huber 1981). In one embodiment, the robustification of the SMILES/discriminant analysis of step 204 is performed using a prospective prediction process in which the above-described SMILES/discriminant analysis is performed where the actual outcome for the $i^{th}$ patient is set arbitrarily to 0.5 (i.e., indeterminate).

The robustified discriminant for this "excised" patient, $\hat{\Delta}_i$, is calculated using the formula $$\hat{\Delta}_i = \Delta_i - \left( \frac{\Delta_i - \hat{\Delta}_i}{1 - h_i} \right) \tag{5}$$

where $\Delta_i$ is determined as described above, and $h_i$ is a proportionality factor (Huber 1981). $\hat{\Delta}_i$ is the fitted discriminant function which can be used in a logistic transformation to determine the retrospective probability of therapeutic outcome, $\hat{Y}_i$, using the formula $$\hat{Y}_i = \frac{1}{1 + e^{I_2 + \delta \hat{\Delta}_i}} \tag{6}$$

where $\delta$ is a statistical parameter and $I_2$ is an intercept. The parameter $\delta$ and intercept $I_2$ are fitted using logistic regression techniques to optimize the calculated probability of response for the $i^{th}$ patient. Alternatively, the prospective probability of treatment outcome, $\hat{\Delta}_i$, can be evaluated using the formula $$\hat{Y}_i = \frac{1}{1 + e^{I_3 + \delta' \hat{\Delta}_i}}. \tag{7}$$

where $\delta'$ a statistical parameter and $I_3$ is an intercept analogous to $\delta$ and $I_2$ discussed above.

The discriminant, $\Delta$ can be evaluated using a neural network representation (Minor and Namini 1996). In addition, it will be appreciated by those of skill in the statistics arts that the discriminant can be generalized to describe outcomes more complex than the binary responder/non-responder outcomes discussed above using a vector representation:

$$\Delta = \begin{pmatrix} \Delta_1 \\ . \\ . \\ . \\ \Delta_n \end{pmatrix}$$

where each of $\Delta_i, \ldots, \Delta_n$ is a discriminant as described above with respect to equations (3) and (4) and n is the number of possible outcomes. This can be performed using either a single multiple-input/multiple-output neural network or n single neural networks.

At this point the model can be evaluated using standard statistical techniques to determine whether the model provides statistically significant prospective predictions. If the model fails to provide such predictions, then a re-evaluation of the assumptions and data can be performed to develop a new model using the methods described above. If the model provides satisfactory performance with respect to prospective predictions, then, referring once more to FIG. 1, step 106 is performed in which the model is tested against an independent data set, i.e., a data set which has not been used to develop the model. At step 108 a second evaluation of the model's performance is made with respect to its ability to predict the likely treatment outcomes of the new data set with statistical significance. At step 110 the confidence in the model is evaluated. If the predictions on the independent data set are not statistically significant, then the model is re-evaluated, beginning at step 102 in which additional or new data is collected. Alternatively, the data can be retained in substantially its original form and the model re-developed at step 104 as described above. If the predictions are statistically significant, then the process of model development is terminated.

The results of the model can be expressed in any format suitable for evaluating a patient's likely response to the modeled treatment regimen. In one embodiment, the results are expressed using a scaled numeric value where 1 denotes the strongest likelihood of response to therapy and 0 denotes the strongest likelihood of non-response to therapy. Scores intermediate 0 and 1 represent an estimated chance of responding (or not responding) to treatment. According to a more particular embodiment, scores greater than about 0.6 on a score range of 0.0 to 1.0 are considered to indicate a likely responders while scores less than about 0.4 are considered to indicate likely non-responders. Scores between 0.4 and about 0.6 are considered to be indeterminate (i.e., the predictive ability of the model for such patients is not significantly different from chance). Other methods for expressing the results of the model will be familiar to those having skill in the statistics and medical arts.

Those having skill in the statistical and medical arts will appreciate that a data set used to describe any medical treatment regimen is unlikely to include all possible presentations of a given disease since one can not be certain that all such presentations are represented in the data set. Thus, for any statistical methodology used to model patient responsiveness to treatment there is an inherent uncertainty as to whether the model has been trained on a data set that is sufficiently large to encompass all likely patients. However, the methods of the present invention described herein provide for a "living" model which is easily and quickly adapted to handle patients that present clinical variables and treatment responses that were not accounted for in the data set used to train the model originally. Data from each of these patients is described as a patient vector and the model is reconfigured using the methods described above to account for this new patient vector. Thus, the predictive power will be seen to improve as the model is used to predict treatment responses for greater numbers of patients.

In another aspect, the present invention includes a method of treating a patient for a disease in accordance with an evaluation of the likely response of the patient to the treatment regimen as determined using a model constructed in accordance with the present invention. According to one embodiment of this aspect of the invention, at least one diagnostic variable relating to a statistical model constructed in accordance with the present invention is applied to the model to obtain a prediction of the patient's likely response to the treatment regimen. The value(s) of the diagnostic variable supplied to the statistical model can be obtained using known methods and materials such as by direct physical examination, biopsy analysis, chemical analysis of samples taken from the patient, family history, or the like. The values so obtained can be supplied to the model in any manner consistent with the presentation of the model. For example, wherein the model is presented as a computer program, the values of the clinical variables can be supplied by key entry, electronic retrieval from a database, pen-based entry, selection made using a key board or touch screen, or the like. In some cases the model may be expressed as a worksheet into which the values of the clinical variables are entered by hand and a result determined by reference to a table of scores or the scores are determined by mathematical calculation such as by use of a hand-held calculator.

After the prediction is obtained it can be used to assist the physician and patient in determining a course of treatment for the patient. The factors in the evaluation will typically include the estimated response of the patient to the treatment regimen in addition to other factors such as age, cost, other conditions for which the patient may be receiving treatment, impact on lifestyle, availability of assistance, and the like. Generally these options are reviewed by the patient in consultation with the clinician. Upon reaching a decision, treatment is performed accordingly. For example, in patients afflicted with AIDS or HIV, treatment options can include the decision to administer a nucleoside analog (e.g., ddI or AZT) or a protease inhibitor to the afflicted patient.

Figure 7A:
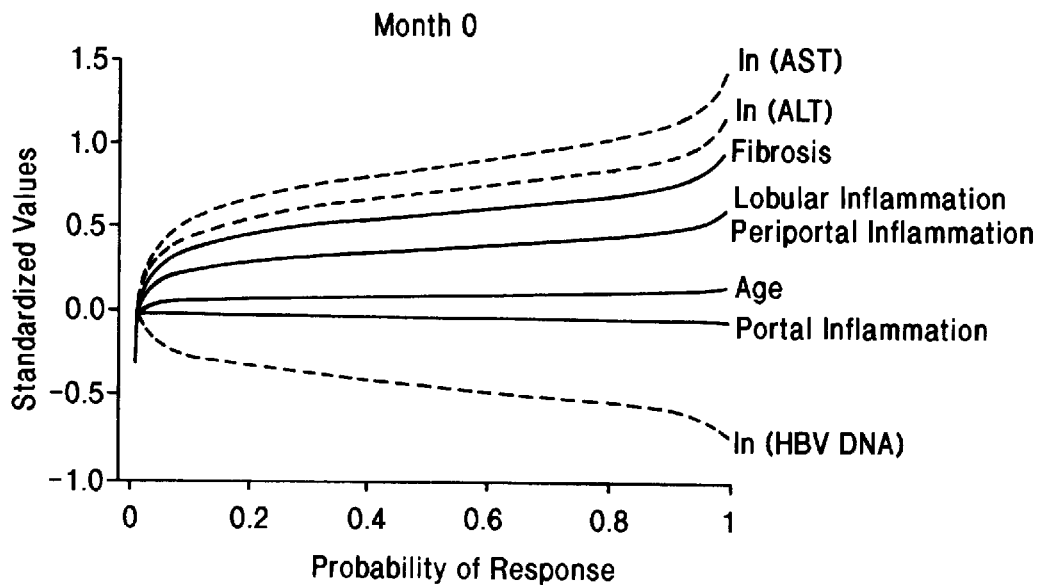
FIGS. 7A and 7B illustrate the use of the method of the invention to understand the relative difference in clinical variables in determining the likely outcome of a therapeutic regimen for treating HBV as a function of time.
Figure 7B:
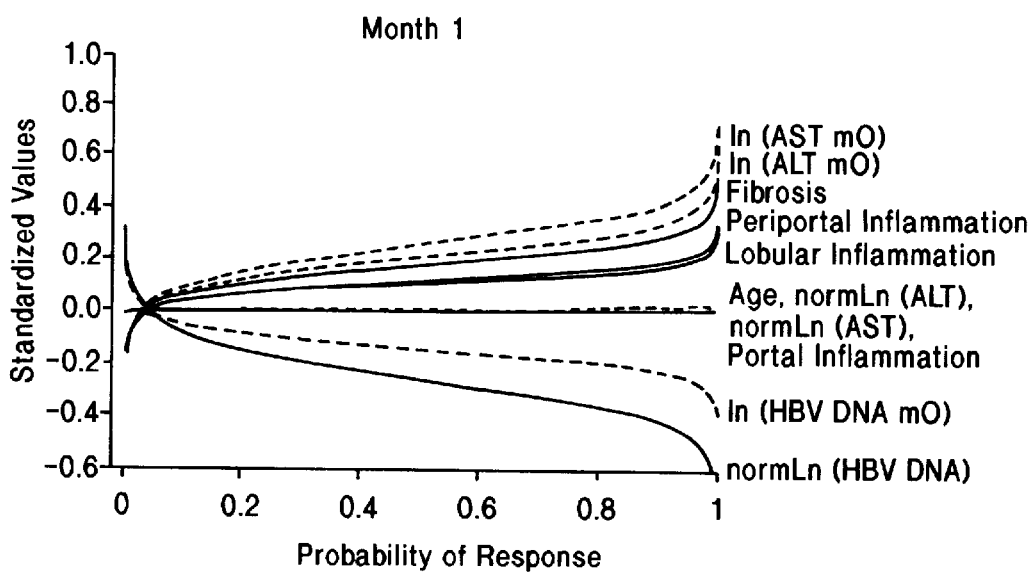

As is well known in the medical arts, the factors that are predictive of a patient's responsiveness to a treatment regimen can change over the course of a disease or the course of treatment. Thus, the particular clinical variables that are most significant for prediction of treatment outcome can change over time. For example, as discussed in greater detail below, the significance of the clinical variables for the prediction of the treatment outcome for treating hepatitis B virus using interferon-α has been found to vary from the beginning of treatment (month 0) to one month of treatment (month 1). As shown in Tables 5 and 6, and in FIGS. 7A and 7B, for predictive models using the method of the invention it was found that at the beginning of treatment (month 0) the degree of fibrosis observed in the patient was ranked as the second most significant clinical variable for the model, while at month 1 fibrosis was ranked as the eighth most significant clinical variable. Also, further predictions made by the model using data obtained after one month were not statistically more reliable than those predictions made at one month. Such information can be important to clinicians and patients in determining which clinical tests to order and which test results to pay closest attention to as indicative of likely treatment outcome or treatment progress.

In addition, the predictive ability of a statistical model may not improve with repeated measurements of the relevant clinical variables over time. For example, the ability of a statistical model to predict the treatment outcome for a patient being treated under a particular treatment regimen may improve with respect to patient data gathered at the outset of treatment versus data gathered at one or more later points during the course of treatment. However, in some cases employment of more recent data in the predictive model does not provide more accurate treatment outcome predictions, i.e., calculating the predicted outcome using data obtained at three months into treatment may not provide a more accurate prediction that using data obtained after one month of treatment. It will be appreciated that asking patients to undergo the time, possible discomfort and/or risk, and expense of additional tests at later points in treatment can be avoided where the additional data gathered will not provide a more accurate assessment of the patient's likely responsiveness to treatment. Thus, having knowledge of period over which the performance of the predictive model can be improved by the gathering of more clinical data can improve patient comfort, reduce patient risk associated with clinical testing (such as from the mortality and morbidity associated with liver biopsies), and reduce costs. Such information is also useful in the pharmaco-economics of the development of new drugs and treatments as the need to obtain expensive test results can be reduced.

These problems are addressed by an embodiment of the present invention in which the above-described methods for developing a treatment prediction model are performed for at least two different time periods and a determination of an optimal testing schedule is made from the models so produced. Such a determination can be made by comparing the predictive abilities of the models produced at the different time periods for which clinical data is obtained and determining which time point, if any, denotes a point at which one or more of the statistically significant clinical variables change between successive models, or a point at which successive models do not provide statistically significant improvements in predictive ability. If such an endpoint is found, then clinicians and patients can determine to change their focus among the clinical variable being monitored, or to forego additional testing past that endpoint with respect to making predictions to treatment outcome. Of course, additional clinical testing may be necessary to monitor and/or determine other treatment issues (e.g., for determining treatment progress).

In some embodiments the present invention employs various process steps involving data stored in, and/or manipulated by, one or more computer systems. These steps require physical manipulation of physical quantities. Usually, though not necessarily, these quantities take the form of electrical or magnetic signals capable of being stored, transferred, combined, compared, and otherwise manipulated. It is sometimes convenient, principally for reasons of common usage, to refer to these signals as bits, values, elements, variables, characters, data structures, or the like. It should be remembered, however, that all of these and similar terms are to be associated with the appropriate physical quantities and are merely convenient labels applied to these quantities.

Further, the manipulations performed are often referred to in terms such as identifying, running, or comparing. In any of the operations described herein that form part of the present invention these operations are machine operations. Useful machines for performing the operations of the present invention include general purpose digital computers or other similar devices. In all cases, there should be borne in mind the distinction between the method of operations in operating a computer and the method of computation itself. The present invention relates to method steps for operating a computer in processing electrical or other physical signals to generate other desired physical signals.

The present invention also relates to an apparatus for performing these operations. This apparatus may be specially constructed for the required purposes, or it may be a general purpose computer selectively activated or reconfigured by a computer program stored in the computer. The processes presented herein are not inherently related to any particular computer or other apparatus. In particular, various general purpose machines may be used with programs written in accordance with the teachings herein, or it may be more convenient to construct a more specialized apparatus to perform the required method steps. The required structure for a variety of these machines will appear from the description given below.

In addition, the present invention further relates to computer readable media which include program instructions for performing various computer-implemented operations. The media and program instructions may be those specially designed and constructed for the purposes of the present invention, or they may be of the kind well known and available to those having skill in the computer software arts. Examples of computer readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that can be executed by the computer using an interpreter.

The computer-implemented methods described herein can be implemented using techniques and apparatus well-known in the computer science arts for executing computer program instructions on computer systems. As used herein, the term "computer system" is defined to include a processing device (such as a central processing unit, CPU) for processing data and instructions that is coupled with one or more data storage devices for exchanging data and instructions with the processing unit, including, but not limited to, RAM, ROM, CD-ROM, hard disks, and the like. The data storage devices can be dedicated, i.e., coupled directly with the processing unit, or remote, i e., coupled with the processing unit, over a computer network. It will be appreciated that remote data storage devices coupled to a processing unit over a computer network can be capable of sending program instructions to a processing unit for execution on a particular workstation. In addition, the processing device can be coupled with one or more additional processing devices, either through the same physical structure (e.g., in a parallel processor), or over a computer network (e.g., a distributed processor.). The use of such remotely coupled data storage devices and processors will be familiar to those of skill in the computer science arts. The term "computer network" as used herein is defined to include a set of communications channels interconnecting a set of computer systems that can communicate with each other. The communications channels can include transmission media such as, but not limited to, twisted pair wires, coaxial cable, optical fibers, satellite links, or digital microwave radio. The computer systems can be distributed over large, or "wide" areas (e.g., over tens, hundreds, or thousands of miles, WAN), or local area networks (e.g., over several feet to hundreds of feet, LAN). Furthermore, various local- and wide-area networks can be combined to form aggregate networks of computer systems. One example of such a confederation of computer networks is the "Internet". The above-described devices and materials will be familiar to those of skill in the computer hardware and software arts.

Figure 6:
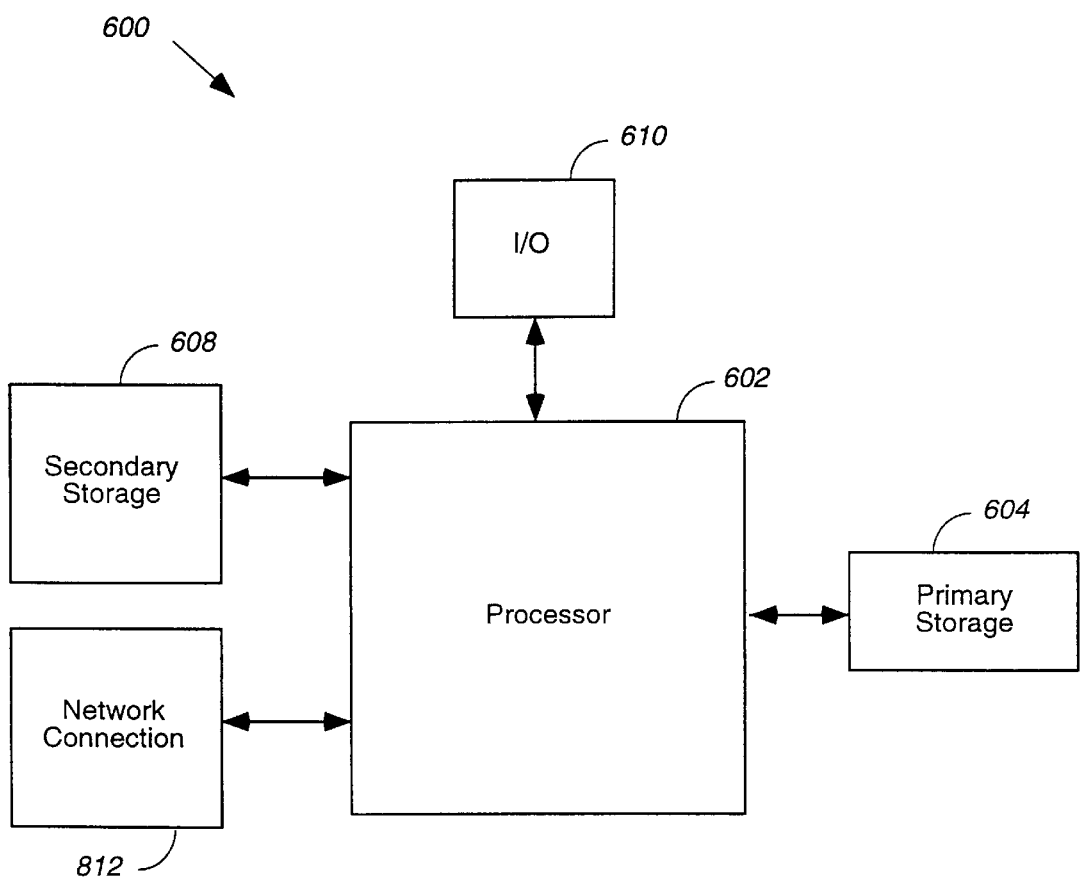
FIG. 6 is a schematic illustration of a computer system in accordance with the present invention.

FIG. 6 at 600 shows a typical computer-based system in accordance with the present invention. The computer includes a processing unit 602 effective for performing computations, such as, but not limited to, a central processing unit (CPU), or multiple processors including parallel processors or distributed processors. Processor 602 is coupled with primary memory 604 such as random access memory (RAM) and read only memory. Typically, RAM includes programming instructions and data, including distributed objects and their associated data and instructions, for processes currently operating on processor 602. ROM typically includes basic operating instructions, data and objects used by the computer to perform its functions. In addition, a secondary storage device 608, such as a hard disk, CD ROM, magneto-optical (floptical) drive, tape drive or the like, is coupled bidirectionally with processor 602. Secondary storage device 608 generally includes additional programming instructions, data and objects that typically are not in active use by the processor, although the address space may be accessed by the processor, e.g., for virtual memory or the like. The above described computer further includes an input/output source 610 that typically includes input media such as a keyboard, pointer devices (e.g., a mouse or stylus) and the like. Computer 600 also includes a network connection 612. Additional mass storage devices (not shown) may also be connected to CPU 602 through network connection 612. It will be appreciated by those skilled in the art that the above described hardware and software elements, as well as networking devices, are of standard design and construction.

EXAMPLES

The following example describes specific aspects of the invention to illustrate the invention and aid those of skill in the art in understanding and practicing the invention. However, this example should not be construed as limiting the invention in any manner.

Analysis of Interferon-α Regimen Outcome Predictors for Treatment of Hepatitis B (HBV)

The above-described methods were applied to determine a model for predicting those HBV patients likely to be responsive Interferon-α (IFNα) treatment. The results obtained using the method of the invention were then compared with a two-stage logistic model of the same treatment regimen on a data set obtained from earlier studies on the effectiveness of IFNα treatments (Hoofnagle, Peters et al. 1988; DiBisceglie, Fong et al. 1993).

Table I lists the variables of clinical data used in the models. These variables were chosen as they represent clinical information commonly recorded for HBV-infected patients considered for therapy and were obtained using standard methods and materials. The clinical variables considered included the serum concentrations of the liver enzymes aminotransferase ([ALT]) and aspartate aminotransferase ([AST]); serum HBV DNA concentrations ([HBV DNA]); measures of histological activity (Knodell scores); age; gender; and interferon dosage. Given that liver biopsies typically are taken at pre-treatment (i.e., month 0), but not after only a single month of therapy (i.e., at month 1), Knodell scores were not available at month 1. Natural log (ln) transforms were applied to all enzyme and HBV DNA concentrations. For the purpose of performing the logarithmic transforms, which require values greater than 0, all serum HBV DNA values below the 0.7 MEq quantification limit of the bDNA assay (available commercially from Chiron Corporation of Emeryville, Calif.) used to determine the HBV DNA levels were set to 0.7 Meq, which are the units employed by the Chiron bDNA assay and imported into the model. Clinical data was available at both month 0 and month 1 for both the liver enzyme and serum HBV DNA measurements. This data was incorporated into the models as the "normalized" natural log which is defined as the ratio of the natural log of the concentration determined at month 1 and the natural log of the concentration determined at month 0. For example, $$\text{Normalized } \ln([AST]) = \ln([AST_1])/\ln([AST_0])$$

where $[AST_1]$ is the concentration of AST at month 1 and $[AST_0]$ is the concentration of AST at month 0. Such ratios reflect the change in these clinical variables in response to treatment and thus provide a measure of the patient's response to interferon treatment.

TABLE 1

| Clinical Variable | Range of Values | Average | Standard Deviation |
|---|---|---|---|
| Liver Enzymes: | | | |
| ln([ALT]) at month 0 (IU/ml) | 3.83–6.50 | 4.91 | 0.58 |
| Normalized ln([ALT]) at month 1 | 0.72–1.25 | 0.99 | 0.11 |
| ln([AST]) at month 0 (IU/ml) | 3.30–6.12 | 4.34 | 0.62 |
| Normalized ln([AST]) at month 1 | 0.76–1.33 | 1.05 | 0.12 |
| bDNA assay results: | | | |
| ln([HBV DNA]) at month 0 (MEq/ml) | 3.72–10.40 | 7.24 | 1.31 |
| Normalized ln([HBV DNA]) at month 1 | −0.10–1.07 | 0.74 | 0.24 |
| Knodell Scores: | | | |
| Periportal inflammation | 1–10 | 4.12 | 2.27 |
| Lobular inflammation | 1–4 | 3.32 | 0.90 |
| Portal inflammation | 0–4 | 1.87 | 1.07 |
| Fibrosis | 0–4 | 2.13 | 1.31 |
| Age (years) | 24.0–70.9 | 40.7 | 11.8 |
| Gender (female = 1, male = 2) | 1,2 | 1.87 | 0.34 |
| Average daily dose of IFNα (MU) | 2.14–5.0 | 4.59 | 0.50 |

To improve robustness and numerical properties, all variables (designated V) were standardized using the equation $V_{st}=(V-\overline{V})/\sigma_v$, where $V_{st}$ is the standardized variable V, $\overline{V}$ is the average value of V, and $\sigma_v$ is the standard deviation with respect to V. For the two-stage logistic regression model, different sets of variables were included at month 0 and month 1. At month 0, the variables used in the model included ln([ALT]), gender, and fibrosis; at month 1 the two-stage logistic regression model included normalized ln([HBV DNA]) at month 1, gender, normalized ln([AST]) at month 1, and fibrosis. All available variables were included in the two-stage SMILES/discriminant logistic regression model of the invention at both month 0 and month 1. Continuous independent variables, such as bDNA assay results and liver enzyme measurements, were used according to the Kshirsager regression method of responder discrimination, whereas categorical independent variables, such as gender, were used to enhance the fit of the Kshirsager regression analysis (Kshirsager 1972). Stepwise regression was performed on the variables shown in Table 1 using known methods (Miller 1990) to determine the minimum set of variables required to produce a model that accurately described the observed responses. In the two-stage logistic analysis, this set comprised clinical variables and their pairwise interactions while for the SMILES method the set comprised all variables for a subset of patients having a minimum number of redundancies (i.e., patients whose clinical profiles were close enough to be defined by the profiles of neighboring patients).

For the two-stage logistic model, regression analysis was performed to determine an optimized estimate of the discriminant function for a given patient j ($\Delta_j$) using the equation $$\Delta_j = I + \sum_{i=1}^{s} w_i V_{ij} \tag{8}$$

where I is the intercept, $V_{ij}$ is the clinical data for patient j, $w_i$ is a weighting parameter, and s is the total number of clinical variables V. To perform the optimization, the intercept I and set of parameters w that minimized the error prediction in the clinical data set were determined using linear regression analysis (Kshirsager 1972). The discriminant function for month 0 for the $j^{th}$ patient was thus found to be:

$$\Delta_j = -0.63 + 0.29 \, [1n(ALT_{0j})] - 0.34 \, G_j + 0.07 \, F_j \tag{9}$$

where $ALT_{0j}$ is the concentration of ALT at month 0, $G_j$ is the gender, and $F_j$ is the fibrosis score for patient j. The discriminant function for month 1 for the $j^{th}$ patient was found to be:

$$\Delta_j = 0.19 - 0.57 \frac{\ln(HBV_{1j})}{\ln(HBV_{0j})} - 0.29 \, G_j + 0.19 \, \ln(ALT_{0j}) + 0.07 \, F_j \tag{10}$$

where $HBV_{0j}$ and $HBV_{ij}$ are the HBV DNA concentrations for patient j at month 0 and month 1 respectively.

Prospective values for each of the discriminant functions of equations (9) and (10) were generated by removing seriatim each patient's outcome from the data set and prospectively calculating a predicted value that discriminated between response and non-response for the excised patient. In this manner a set of prospective discriminant values was determined for the second stage of the analysis in which a logistic transformation was used to convert the above-described discriminant functions into corresponding probabilities. This was performed by determining the values of $I_2$ and m for the equation $$Y_j = \frac{1}{1 + e^{I_2 + m\Delta_j}} \tag{11}$$

which was optimized using conventional methods for the calculated probability of response for patient j who had been removed from the data set. The probabilities for response for month 0 and month 1 for the $j^{th}$ patient were thus determined by substituting equations (9) and (10) into equation (11) and performing the optimization which yielded the equations:

$$Y_j = \frac{1}{1 + e^{2.37 - 4.48\Delta_j}} \text{ and} \tag{12}$$

$$Y_j = \frac{1}{1 + e^{2.37 - 4.60\Delta_j}} \tag{13}$$

respectively.

Using the method of the invention as described above, the above-referenced patient data was processed to provide a statistical model for predicting the therapeutic outcome of IFNα treatment. The final, robustified model comprised the intercept and a parsimonious "basis set" of patient vectors shown in Table 2 below, along with their associated coefficients and measures of statistical significance. The quantities labelled "$NN_i$" are the individual patients in the data set.

TABLE 2

| Patient Vector ($NN_1$) | Estimated $C_{NNj}$ | Std. Error | Prob. \|t\| |
|---|---|---|---|
| Intercept | 0.0020727 | 0.025284 | 0.9347 |
| NN61 | 1.3720159 | 0.669977 | 0.0418 |
| NN62 | -14.29 | 2.805759 | 0.0000 |
| NN65 | -2.467209 | 0.65611 | 0.0002 |
| NN5 | 3.3553535 | 0.887975 | 0.0002 |
| NN55 | -5.101133 | 1.396477 | 0.0003 |
| NN34 | -1.92533 | 1.698705 | 0.0003 |
| NN17 | 1.3228189 | 0.344411 | 0.0002 |
| NN47 | 0.5787614 | 0.28874 | 0.0463 |
| NN12 | 7.4519035 | 1.706147 | 0.0000 |
| NN15 | 0.5978779 | 0.277224 | 0.0322 |
| NN18 | 2.9009328 | 1.145815 | 0.0121 |
| NN13 | 0.6390905 | 0.69168 | 0.0002 |
| NN41 | -5.199659 | 1.276955 | 0.0001 |
| NN19 | 1.7248308 | 0.396002 | 0.0000 |
| NN73 | 2.6045263 | 0.779973 | 0.0010 |
| NN81 | -0.810685 | 0.404368 | 0.0462 |
| NN8 | 1.9642731 | 0.540413 | 0.0003 |
| NN22 | 13.475018 | 2.750663 | 0.0000 |
| NN23 | 0.5444819 | 0.249596 | 0.0302 |
| NN51 | -3.008566 | 0.85545 | 0.0005 |
| NN24 | 1.8685842 | 0.589329 | 0.0017 |
| NN25 | 1.7516871 | 0.507745 | 0.0007 |
| NN77 | -3.26829 | 0.73523 | 0.0000 |
| NN78 | 1.027411 | 0.479296 | 0.0332 |
| NN26 | 3.2843914 | 0.981426 | 0.0010 |
| NN79 | -1.832889 | 0.756379 | 0.0162 |
| NN80 | -3.2893914 | 0.697238 | 0.0000 |
| NN82 | -1.323037 | 0.440732 | 0.0030 |
| NN10 | 4.7368318 | 1.284708 | 0.0003 |
| NN91 | -2.288321 | 0.707159 | 0.0014 |
| NN14 | 1.5273388 | 0.486007 | 0.0019 |
| NN33 | -2.169852 | 0.616879 | 0.0005 |

Using the patient vectors listed above, the probabilities for response at month 0 and month 1 for patient j were determined to be:

$$Y_j = \frac{1}{1 + e^{6.80 - 13.49\Delta_j}} \text{ and} \tag{14}$$

$$Y_j = \frac{1}{1 + e^{8.99 - 18.31\Delta_j}}. \tag{15}$$

The predictive results for both methodologies for the prospective case (described above) and the retrospective case (i.e., on a set of unrelated data) are provided in Table 3 below. A total of 83 data points were included in these analyses; the results are shown as the percentage of correct predictions with the parameters for month 0 and month 1. The two-stage logistic regression model predicted (prospectively) 61% of the responders and 76% of the non-responders correctly at month 0. A higher rate of prediction of responders was obtained at month 1 (69% correct), but no improvement was found for the prediction of non-responders (77% correct). In contrast, the SMILES method yielded higher prediction rates among both responders and non-responders at both time points: 77% correctly predicted responders and 87% correctly predicted nonresponders at month 0; and 86% of responders and 92% of non-responders predicted correctly at month 1.

As indicated in Table 3, the relative improvement by the SMILES method over the two-stage logistic regression model was greatest with respect to the prospective prediction of responders, particularly when the month 1 variables were considered. For comparison, the retrospective percentage of predicted correct for both prognostic models was determined. These results are shown on the left-hand side of the Table. As expected, the retrospective values predicted correctly were higher for responders and non-responders for both models. Of course, given that retrospective analyses are fitted to the data sets from which they are derived, these values do not necessarily provide realistic prediction results. More realistic prediction results are provided by the more robust prospective analyses. Nevertheless, the SMILES model provided remarkable accuracy in predicting correctly 92% of responders and 97% of non-responders at month 0, and 96% of responders and 97% of non-responders at month 1.

TABLE 3

|  | Percentage of Correctly Predicted Prospective | | Percentage of Correctly Predicted Retrospective | |
| --- | --- | --- | --- | --- |
|  | Responders | Non-Responders | Responders | Non-Responders |
| Arbitrary Prediction | 33 | 67 | N/A | N/A |
| Two-Stage Logistic Regression: | | | | |
| Month 0 | 61 | 76 | 71 | 80 |
| Month 1 | 69 | 77 | 71 | 78 |
| Method of the Invention: | | | | |
| Month 0 | 77 | 87 | 92 | 95 |
| Month 1 | 86 | 92 | 96 | 97 |

The numbers of patients and the corresponding error rates within each of the probability of response ranges defined by probabilities less than 0.2 (strong likelihood of no response), greater than 0.8 (strong likelihood of response) and 0.2–0.8 (indeterminate) are given in Table 4 for both the two-stage model and the model developed using the method of the invention. The results show that the overall error rate of the two-stage logistic regression model at low (<0.20) probability of response at month 0 was about 6%, indicating that patients ultimately have only about a 6% chance of being a responder. At the indeterminate range (0.20–0.80), the probability of response at month 0 had an overall error rate was about 40%, indicating that in this range of probability of response are little better than tossing a coin. At a high (>0.80) probability of response, too few patients were available from the data set to make a statistically significant determination of the error rates (ND).

TABLE 4

| | Probability of Response | | |
| --- | --- | --- | --- |
| | <0.2 | 0.2–0.8 | >0.8 |
| Two-stage model at month 0 | | | |
| Number of patients | 31 | 49 | 2 |
| Error rate | 6% | 37% | ND |
| Two-stage model at month 1 | | | |
| Number of patients | 33 | 44 | 5 |
| Error rate | 6% | 41% | ND |
| SMILES model at month 0 | | | |
| Number of patients | 44 | 32 | 6 |
| Error rate | 5% | 38% | ND |
| SMILES model at month 1 | | | |
| Number of patients | 49 | 16 | 17 |
| Error rate | 2% | 31% | 6% |

As with the data in Table 1 above, there was no improvement in the overall error rates of the two-stage logistic regression model for low and indeterminate probabilities of response at month 1 as compared to month 0 (about 6% and about 40%, respectively). However, at the high probability of response range 5 of 5 patients were predicted correctly as responders, implying that the two-stage logistic regression model at month 1 performs well in this range. These results indicate that the two-stage logistic model performs well for the prediction of non-responders with low probability of response at both month 0 and month 1, as well as for the prediction of responders with high probability of response at month 1. However, the two-stage logistic regression model is limited in its ability to predict the response of patients in the mid-range of probability of response. Unfortunately, the majority of patients were classified in the mid-range probability of response by the two-stage logistic regression model (49 of 82 at month 0 and 44 of 82 at month 1).

More reliable predictions were obtained with the SMILES method as evidenced both by lower overall error rates, particularly at month 1, as well an increased distribution of patients into the low and high probabilities of response ranges and out of the mid probability of response range. At month 0, the error rates for the low- and indeterminate-range probabilities of response were similar to that of the two-stage logistic regression model (5% and about 40% respectively). However, more patients were classified in the low probability of response range and fewer in the mid probability of response range as compared to the two-stage logistic regression model at month 0. In the high probability of response range, 6 of 6 patients were correctly predicted as responders implying that the SMILES method at month 0 performs well in this range.

At month 1, overall error rates for the SMILES method were lower for both the low and indeterminate probability of response ranges, dropping to 2% and about 30% respectively. In addition, even more patients were distributed into the low and high probability of response ranges, and fewer patients were classified in the indeterminate probability range, by the SMILES method at month 1. The performance of the SMILES method also was better than that of the two-stage logistic regression model in the prediction of responders with high probability of response at month 1. With 16 of 17 patients classified at better than 0.80 probability of response predicted correctly by the SMILES method as responders, the error rate was only 6%. This indicates that a patient predicted in the range of likely responders by the SMILES method at month 1 ultimately has a 94% chance of actually being a responder.

The better performance of the SMILES method also can be seen in the more accurate prediction of individual patients. Table 5 lists the prospective predictions and clinical profiles of 8 individual patients, including 6 responders and 2 nonresponders ($M_0$ and $M_1$ indicate Month 0 and Month 1 respectively, "AST" indicates ln([AST]), "HBV" indicates ln([HBV DNA]), and "Fib" indicates Fibrosis). This subset of 8 patients was the most difficult group of patients for the two-stage model to predict at month 0, classified within the range of 0.45 to 0.55 probability of response. Since these 8 patients fell clearly within the indeterminate probability of response range, the two-stage logistic model was unable to predict whether these patients would be responders or nonresponders at month 0. For all patients except one (patient 23), the predictions of the two-stage logistic model at month 1 were not improved over those at month 0. The two-stage logistic regression model did predict a higher probability of response at month 1 for patient 23, a patient who ultimately did respond to IFNα treatment. However, the two-stage logistic regression model also predicted a lower probability of response at month 1 for patient 10—who also ultimately was a responder. Hence, the predictions of the two-stage model for most of these 8 patients were ambiguous at best, and incorrect at worst.

TABLE 5

| Patient ID | Two-Stage Logistic Model | | SMILES Model | | AST | HBV | Fib. |
|---|---|---|---|---|---|---|---|
| | $M_0$ | $M_1$ | $M_0$ | $M_1$ | $M_0$ | $M_0$ | |
| Responders | | | | | | | |
| 7 | 0.46 | 0.53 | 0.95 | 0.91 | 4.45 | 5.84 | 1 |
| 10 | 0.45 | 0.27 | 0.96 | 0.94 | 4.39 | 6.07 | 4 |
| 11 | 0.51 | 0.45 | 0.91 | 1.00 | 5.20 | 5.44 | 4 |
| 23 | 0.53 | 0.80 | 0.89 | 0.99 | 5.48 | 6.44 | 3 |
| 26 | 0.48 | 0.39 | 0.70 | 1.00 | 5.63 | 7.11 | 3 |
| 29 | 0.50 | 0.54 | 0.77 | 0.99 | 4.67 | 8.59 | 3 |
| Non-Responders | | | | | | | |
| 45 | 0.50 | 0.45 | 0.32 | 0.25 | 5.18 | 6.18 | 1 |
| 51 | 0.48 | 0.35 | 0.42 | 0.89 | 5.12 | 7.07 | 3 |

By contrast, the predictions made using the SMILES method for all 8 patients at month 0 were accurate, with 6 of 6 patients correctly predicted to be responders; and 2 of 2patients correctly predicted to be nonresponders. The predictions were even better at month 1, with 7 of the 8 patients being predicted correctly. However, the SMILES method incorrectly predicted a higher probability of response for patient 51 who ultimately was a nonresponder. Nevertheless, the predictions made using the SMILES method were correct for most of these 8 patients at both month 0 and month 1, even in the absence of any clear univariate trends among the clinical variables.

Predictions made using the SMILES method for a sequence of patients with increasing probability of response is illustrated in FIG. 7. For ease of comparison, clinical variables were standardized to have the same origin and scale as indicated on the y-axis. In this illustration, the common origin (i.e., zero) is the average value for each standardized clinical variable, and the common scale is defined in units of the standard deviation for each clinical variable allowing direct comparison between different clinical variables. Comparison of data for responders versus nonresponders indicates that a patient with the highest probability of response has a clinical profile such that the values of the clinical variables are farthest from the average of the data set. Conversely, a patient with the lowest probability of response has a clinical profile such that the values of the clinical variables are closest to the average of the data set.

At both month 0 (FIG. 7A) and month 1 (FIG. 7B), patients with the highest probability of response have higher than average values for liver enzymes (AST and ALT) and three of the four components of the Knodell score (fibrosis, lobular inflammation and periportal inflammation), and have lower than average values for HBV DNA levels. Hence, these clinical variables are most useful in distinguishing between non-response and response. A subset of clinical variables (portal inflammation, age, normalized AST and ALT at month 1) show close to average values for both nonresponding and responding patients.

The month 1 model differs from the month 0 model in there being less dispersion between standardized clinical variables for patients with indeterminate probabilities of responsiveness. For example, at the 50% probability of response point, values ranged approximately from −0.2 to 0.5 at month 0, but only from −0.3 to 0.3 at month 1. This smaller dispersion of the standardized clinical variables at month 1 illustrates the greater sensitivity of the SMILES method in predicting response at month 1 as compared to month 0. Hence, the additional clinical information available at month 1 improves the prediction of response.

The relative contribution of each clinical variable to the two-stage logistic regression and the SMILES regression models of the present invention was evaluated by the virtual parameter method to determine which clinical variable(s) most influenced the determination of likely response. This analysis was performed using the following method. A "virtual parameter" $\alpha_i$, set equal to unity, was assigned to each clinical variable $P_i$ for each patient vector. The effect of each virtual parameter was determined for the resulting discriminant function, $\Delta_i(\alpha_i, P_i)$, by determining the partial derivative $$\partial \Delta_i(\alpha_i, P_i)/\partial \alpha_i$$

to obtain thereby a resulting vector of partial derivatives corresponding to each patient vector. From this resulting vector a matrix was constructed that comprised the sum of the outer product of each resulting vector for each patient. The matrix was inverted, and the diagonal elements of the inverted matrix were multiplied by $\sigma^2$, the sum of the squared residuals for $\Delta$ divided by the number of patients to obtain an approximate F distribution. From the F distribution the approximate p-values for each clinical variable could be determined using standard methods to obtain a ranking of the significance of each of the clinical variable used in the model.

The results are shown in Table 6 and Table 7 below for the two-stage model (Table 6) and the SMILES method (Table 7). Referring to Table 6, at month 0, the clinical variable having the greatest impact on the prediction results of the two-stage logistic regression model was ln([ALT]). Gender and fibrosis also were important for the prediction results of the two-stage logistic regression model, while variables such as serum HBV DNA levels and other measures of histological activity did not impact the model at month 0 to a statistically significant degree. At month 1, normalized ln([HBV DNA]) had the greatest impact on the prediction results of the two-stage logistic regression model. ln([ALT]) at month 0, gender and fibrosis also remained important variables for the prediction results of the two-stage logistic regression model at month 1.

TABLE 6

| | Month 0 | | Month 1 | |
|---|---|---|---|---|
| Ranking | Clinical Variable | Approximate p Value | Clinical Variable | Approximate p Value |
| 1 | ln([ALT]) at month 0 | 0.0007 | Normalized ln ([HBV DNA]) | 0.004 |
| 2 | Gender | 0.012 | ln([ALT]) at month 0 | 0.027 |
| 3 | Fibrosis | 0.040 | Gender | 0.028 |
| 4 | N/A | N/A | Fibrosis | 0.051 |

Interesting trends were noted in the relative importance of clinical variables at month 0 versus month 1 for the model of the present invention (Table 7). Measures of AST and HBV DNA had the greatest impact on the model at both month 0 and month 1, indicating that measurement of these two variables is important for prediction at both time points. In addition, at month 1 the normalized AST, ALT, and HBV DNA values most impacted the model, indicating that all three of the clinical variables were important in predicting response. In evaluating the relative importance of clinical variables in the model, it is important to keep in mind that the p values shown for individual variables have taken into account not only the effect of the variable itself but also the synergistic effects of the variable in combination with other variables in the clinical data set as discussed above. In general, it will be appreciated that it is possible for the correlation between a variable and response to be near zero; yet that variable may nonetheless be useful in predicting response through synergistic effects in combination with other variables that are important to predicting response.

TABLE 7

| | Month 0 | | Month 1 | |
|---|---|---|---|---|
| Ranking | Clinical Variable | Approximate p Value | Clinical Variable | Approximate p Value |
| 1 | ln([AST]) at month 0 | 0.0002 | Normalized ln([AST]) | 0.003 |
| 2 | Fibrosis | 0.002 | Normalized ln([ALT]) | 0.004 |
| 3 | ln([HBV DNA]) at month 0 | 0.002 | Normalized ln ([HBV DNA]) | 0.033 |
| 4 | ln([ALT]) at month 0 | 0.011 | ln([AST]) at month 0 | 0.038 |
| 5 | Portal Inflammation | 0.012 | ln([ALT]) at month 0 | 0.061 |
| 6 | Periportal Inflammation | 0.012 | Gender | 0.064 |
| 7 | Gender | 0.019 | Age | 0.066 |
| 8 | Lobular Inflammation | 0.051 | Fibrosis | 0.079 |
| 9 | Age | 0.056 | Portal Inflammation | 0.095 |
| 10 | Dosage | 0.073 | Dosage | 0.101 |
| 11 | | | Lobular Inflammation | 0.160 |
| 12 | | | ln([HBV DNA]) at month 0 | 0.162 |
| 13 | | | Periportal Inflammation | 0.190 |

Thus, from the foregoing it will be appreciated that the methods, software and apparatus described herein provide statistical models of patient response to therapeutic treatments that are more accurate and more robust than heretofore available. Using the methods, software, and apparatus described herein, clinicians and patients can make more informed treatment decisions based, at least in part, on the estimates of treatment response provided by the present invention.

Although certain embodiments and examples have been used to describe the present invention, it will be apparent to those having skill in the art that various changes can be made to those embodiment and/or examples without departing from the scope or spirit of the present invention.

The following materials are incorporated herein by reference in their entirety for all purposes.

Blumberg, B. S. 1994. "Complexity and the Hepatitis Viruses." *Gut* 35: 1770–1771.

Coveney, P. and R. Highfield. *Frontiers of Complexity The Search for Order In a Chaotic World.* New York. Fawcett Columbine.

DiBisceglie, A. M., T. -L. Fong, et al. 1993. "A Randomized, Controlled Trial of Recombinant α-Interferon Therapy for Chronic Hepatitis B." *Journal of Gastroenterology* 88(11): 1887–1892.

Dillon, W. R. and A. Goldstein. 1984. *Multivariate Analysis Methods and Applications.* New York. John Wiley & Sons.

Hoofnagle, J. H., M. Peters, et al. 1988. "Randomized, Controlled Trial of Recombinant Human α-Interferon In Patients With Chronic Hepatitis B." *Gastroenterology* 95: 1318–1325.

Huber, P. J. 1981. *Robust Statistics.* New York. John Wiley & Sons.

Kshirsager, A. M. 1972. *Multivariate Analysis.* Marcel Dekker.

Miller, A. J. 1990. *Subset Selection in Regression.* London. Chapman and Hall.

Minor, J. M. 1996. "Generalized Ridge Analysis With Application to Population Pharmacokinetics/Dynamics." *J. Biopharm. Statist.* 6: 105–114.

Minor, J. M. and H. Namini 1996. "Analysis of Clinical Data Using Neural Nets." *J. Biopharm. Statist.* 6: 83–104.

What is claimed:

1. A method for evaluating the utility of a treatment regimen for treating a disease for the application of such treatment to a patient having such disease, the method comprising the steps of:

a) determining at least one diagnostic variable relating to a statistical model describing the utility of said treatment regimen, said statistical model being derived by the steps of i) developing a discriminant function which is effective for classifying the response of individuals afflicted with said disease to said treatment regimen, said discriminant function being based at least in part on a data set including clinical profiles of individual patients who have been treated for said disease using said treatment regimen, said clinical profiles of individual patients including said diagnostic variable; and ii) performing a logistic regression using said discriminant function to assign thereby a probability of treatment outcome for said individuals; and b) applying said diagnostic variable to said statistical model to obtain an estimate of the utility of said treatment regimen for the treatment of said disease in said patient.

2. The method of claim 1, wherein said estimate comprises a projected likely treatment outcome score.

3. The method of claim 2, further including the step of treating said patient for said disease in accordance with said determination of the utility of said treatment regimen.

4. The method of claim 3, wherein said treatment outcome score comprises a value selected from a set of values that form a treatment outcome scale, said treatment outcome scale including a likely success region, a likely failure region, and an intermediate region.

5. The method of claim 3, wherein said discriminant function comprises a polynomial function.

6. The method of claim 3, wherein said discriminant function is developed using a similarity-metric least squares (SMILES) analysis of said data set.

7. The method of claim 6, wherein said derivation of said statistical model includes the additional step of performing a prospective prediction using said data set.

8. The method of claim 7, wherein said disease is selected from the group consisting of AIDS, HBV, and HCV.

9. The method of claim 8, wherein said disease is HBV.

10. A method for producing a statistical model of a likely response to a treatment regimen for treating a disease in a mammal, the method comprising the steps of:

a) obtaining at least one sample population of individuals representative of said disease, said sample population being treated for said disease using said treatment regimen for treating said disease;

b) determining from said sample population a set of data for at least one variable relating to said population, said disease, or said regimen, said variable having a putative correlation with said regimen for treating said disease;

c) deriving from said set of data said statistical model of said likely response to said regimen for treating said disease, wherein said step of deriving includes the sub-steps of:

i) standardizing said data;

ii) developing a discriminant function which is effective for classifying the response of individuals afflicted with said disease to said treatment regimen, said discriminant function being based at least in part on clinical profiles of individual patients who have been treated for said disease using said treatment regimen, said clinical profiles of individual patients including said diagnostic variable; and iii) performing a logistic regression using said discriminant function to assign thereby a probability of treatment outcome for said individuals.

11. The method of claim 10, wherein said sub-step of standardizing said data includes the sub-steps of:

a) determining the mean and the standard deviation for said set of data;

b) subtracting said mean from said data; and c) dividing the result of sub-step b) by said standard deviation to produce thereby a set of normalized data.

12. The method of claim 11, further including the step of performing an outlier analysis of said set of normalized data.

13. The method of claim 10, wherein said discriminant function includes a polynomial function.

14. The method of claim 10, wherein said discriminant function is derived from a similarity-metric least squares (SMILES) analysis of said data set.

15. The method of claim 14, wherein a) said SMILES analysis includes the sub-steps of:

i) defining a set of patient vectors which includes said data;

ii) defining a node from said set of patient vectors;

iii) determining a distance from each of said patient vectors to each of said nodes to derive thereby a set of distances;

iv) determining a set of similarity values using said set of distances;

v) regressing on said set of similarity values to obtain thereby a set of predicted outcome values and a set of weighting coefficients; and vi) regressing on said set of predicted outcome values and set of weighting coefficients to provide thereby said robustified model; and b) said method further includes the steps of i) robustifying said statistical model; and ii) performing a prospective prediction with said statistical model using said data set.

16. The method of claim 15, wherein said step of robustifying includes performing a Ridge regression on said set of predicted outcome values and said set of weighting coefficients.

17. The method of claim 15, wherein said set of similarity values are derived from a monotonic, decreasing function.

18. The method of claim 17, wherein said monotonic, decreasing function has the mathematical form:

$$f(D_{ij}) = \frac{1}{D_{ij} + \epsilon}$$

where $D_{ij}$ is the distance from the $i^{th}$ data point to the $j^{th}$ node and $\epsilon$ is a parameter.

19. The method of claim 17, wherein said monotonic, decreasing function has the mathematical form:

$$f(D_{ij}) = \beta e^{-\alpha D_{ij}^2} + \gamma$$

where $D_{ij}$ is the distance from the $i^{th}$ data point to the $j^{th}$ node and $\alpha$, $\beta$, and $\gamma$ are parameters.

20. The method of claim 17, wherein said monotonic, decreasing function has the mathematical form:

$$f(D_{ij}) = \frac{1}{1 + \beta e^{\alpha D_{ij} + \gamma}}$$

where $D_{ij}$ is the distance from the $i^{th}$ data point to the $j^{th}$ node and $\alpha$, $\beta$, and $\gamma$ are parameters.

21. The method of claim 20, wherein $\alpha$ is chosen such that the square of the standard deviation of said data is about 1.5n, where n is the number of variables in said statistical model.

22. A method for optimizing testing schedules for determining the efficacy of a regimen for treating a disease in a mammal, the method comprising the steps of evaluating a statistical model describing said treatment regimen for at least two time periods, said statistical model being derived using the method of claim 10 to determine thereby said optimal testing schedule for determining the efficacy of said method.

23. The method of claim 22, wherein said disease is selected independently from the group selected independently from the group consisting of AIDS, HBV, and HCV.

24. The method of claim 23, wherein said disease is HBV.

25. The method of claim 24, wherein said statistical model is derived using a SMILES analysis of said data set.

26. A computer system for producing a statistical model of a regimen for treating a disease in a mammal using a set of data derived from at least one sample population of individuals representative of said disease, said sample population being treated for said disease using a treatment regimen for treating said disease, the system comprising:
   a) a pre-processing mechanism for standardizing said set of data to produce a set of normalized data; and
   b) a processing mechanism for processing said standardized data, said processing mechanism configured to
      i) develop a discriminant function which is effective for classifying the response of individuals afflicted with said disease to said treatment regimen, said discriminant function being based at least in part on clinical profiles of individual patients who have been treated for said disease using said treatment regimen, said clinical profiles of individual patients including said diagnostic variable; and
      ii) perform a logistic regression using said discriminant function to assign thereby a probability of treatment outcome for said individuals.

27. The computer system of claim 26, wherein said pre-processing mechanism for standardizing said data is configured to:
   a) determine the mean and the standard deviation for said set of data;
   b) subtract said mean from said data; and
   c) divide the result of sub-step b) by said standard deviation to produce thereby a set of normalized data.

28. The computer system of claim 27, wherein said pre-processing mechanism is further configured to perform an outlier analysis of said set of normalized data.

29. The computer system of claim 28, wherein said pre-processing mechanism is further configured to augment said set of normalized data with null data.

30. The computer system of claim 26, wherein said pre-processing mechanism is further configured to augment said set of normalized data with null data.

31. The computer system of claim 30, wherein said processing mechanism is configured to perform a similarity-metric least squares (SMILES) analysis including:
   a) defining a node for each of said data;
   b) determining a distance from each point of said set of data to each of said nodes to derive thereby a set of distances;
   c) determining a set of similarity values using said set of distances;
   d) regressing on said set of similarity values to obtain thereby a set of predicted outcome values and a set of weighting coefficients; and
   e) regressing on said set of predicted outcome values and set of weighting coefficients to provide thereby said robustified model.

32. The computer system of claim 31, wherein said processing mechanism is configured to perform a Ridge regression on said set of predicted outcome values and said set of weighting coefficients.

33. The computer system of claim 32, wherein said set of similarity values are derived from a monotonic, decreasing function.

34. The computer system of claim 33, wherein said monotonic, decreasing function has the mathematical form:

$$f(D_{ij}) = \frac{1}{1 + \beta e^{\alpha D_{ij} + \gamma}}$$

where $D_{ij}$ is the distance from the $i^{th}$ data point to the $j^{th}$ node and $\alpha$, $\beta$, and $\gamma$ are parameters.

35. A computer system for evaluating the utility of a treatment regimen for treating a disease for the application of such treatment to a patient having such disease, said computer system comprising a processor configured to process at least one diagnostic variable obtained from said patient relating to a statistical model describing the utility of said treatment regimen, said statistical model being derived using the method of claim 10, to produce thereby an estimate of the utility of said treatment regimen for the treatment of said disease in said patient.

36. The computer system of claim 35, wherein said estimate comprises a projected likely treatment outcome score.

37. The computer system of claim 36, wherein said treatment outcome score comprises a value selected from a set of values that form a treatment outcome scale, said treatment outcome scale including a likely success region, a likely failure region, and an intermediate region.

38. The computer system of claim 37, wherein said statistical model includes a discriminant function which includes a polynomial function.

39. The computer system of claim 38, wherein said statistical model includes a discriminant function which is derived from a similarity-metric least squares (SMILES) of said data set.

40. The computer system of claim 39, wherein said disease is selected from the group consisting of AIDS, HBV, and HCV.

41. The computer system of claim 40, wherein said disease is HBV.

42. A computer system for optimizing testing schedules for determining the efficacy of a regimen for treating a disease in a mammal, the computer system comprising a processor configured to evaluate a statistical model describing said treatment regimen for at least two time periods, said statistical model being derived using the method of claim 10, to provide thereby said optimized testing schedule for determining the efficacy of said method.

43. The computer system of claim 42, wherein said disease is selected independently from the group selected independently from the group consisting of AIDS, HBV, and HCV.

44. The computer system of claim 43, wherein said disease is HBV.

45. A computer program product including a computer-readable medium having computer-readable program code devices embodied therein for producing a statistical model of a regimen for treating a disease in a mammal using data obtained from at least one sample population of individuals representative of said disease, said sample population being treated for said disease using said treatment regimen, said program code devices being configured to cause a computer to perform the steps of:
   a) standardizing said data to produce standardized data;

b) processing said standardized data to develop a discriminant function which is effective for classifying the response of said individuals to said treatment regimen, said discriminant function being based at least in part on clinical profiles of individual patients who have been treated for said disease using said treatment regimen, said clinical profiles of individual patients including said diagnostic variable; and c) performing a logistic regression using said discriminant function to assign thereby a probability of treatment outcome for said individuals.

46. The computer program product of claim 45, wherein said program code devices are further configured to cause a computer to perform the sub-steps of:

a) determining the mean and the standard deviation for said set of data;

b) subtracting said mean from said data; and c) dividing the result of sub-step b) by said standard deviation to produce thereby a set of normalized data.

47. The computer program product of claim 46, wherein said program code devices are further configured to cause a computer to perform an outlier analysis of said set of normalized data.

48. The computer program product of claim 47, wherein said program code devices are further configured to cause a computer to perform augmenting said set of normalized data with null data.

49. The computer program product of claim 46, wherein said program code devices are further configured to cause a computer to perform augmenting said set of normalized data with null data.

50. The computer program product of claim 49, wherein said program code devices are further configured to cause a computer to perform a similarity-metric least squares (SMILES) analysis of said standardized data, said SMILES analysis including the sub-steps of:

a) defining nodes from said data;

b) determining a distance from each point of said set of data corresponding to an individual who has been treated using said treatment regimen to each of said nodes to derive thereby a set of distances;

c) determining a set of similarity values using said set of distances;

d) regressing on said set of similarity values to obtain thereby a set of predicted outcome values and a set of weighting coefficients; and e) regressing on said set of predicted outcome values and set of weighting coefficients to provide thereby said robustified model.

51. The computer program product of claim 50, wherein said program code devices are further configured to cause a computer to perform a Ridge regression on said set of predicted outcome values and said set of weighting coefficients.

52. The computer program product of claim 51, wherein said set of similarity values are derived from a monotonic, decreasing function.

53. The computer program product of claim 52, wherein said monotonic, decreasing function has the mathematical form:

$$f(D_{ij}) = \frac{1}{1 + \beta e^{\alpha D_{ij} + \gamma}}$$

where $D_{ij}$ is the distance from the $i^{th}$ data point to the $j^{th}$ node and $\alpha$, $\beta$, and $\gamma$ are parameters.

54. A computer program product including a computer-readable medium having computer-readable program code devices embodied therein for evaluating the utility of a treatment regimen for treating a disease for the application of such treatment to a patient having such disease, said program code devices being configured to cause a computer to process at least one diagnostic variable relating to a statistical model describing the utility of said treatment regimen, said statistical model being derived using the method of claim 10, to determine thereby the utilit of said treatemnt regimen for treating said patient.

55. The computer program product of claim 54, wherein said program code devices are configured to cause said computer to determine a projected likely treatment outcome score.

56. The computer program product of claim 55, wherein said statistical model includes a discriminant function derived from a similarity-metric least squares (SMILES) analysis of said data set.

57. The computer program product of claim 56, wherein said disease is selected from the group consisting of AIDS, HBV, and HCV.

58. The computer program product of claim 57, wherein said disease is HBV.

59. A computer program product including a computer-readable medium having computer-readable program code devices embodied therein for optimizing testing schedules for determining the efficacy of a regimen for treating a disease in a mammal, said program code devices being configured to cause a computer to evaluate a statistical model describing said treatment regimen for at least two time periods, said statistical model being derived using the method of claim 10, to determine thereby said optimal testing schedule for determining the efficacy of said method.

60. The computer program product of claim 59, wherein said disease is selected independently from the group selected independently from the group consisting of AIDS, HBV, and HCV.

61. The computer program product of claim 60, wherein said disease is HBV.

62. A method for treating a disease in a patient having such disease, the method comprising the steps of:

a) applying at least one diagnostic variable relating to a statistical model describing the likely response of a patient to said treatment regimen, said statistical model being derived using the method of claim 10, to obtain thereby a prediction of patient response to said treatment regimen;

b) evaluating said estimate to determine a course of treatment for said patient; and c) treating said patient for said disease in accordance with said determination.

63. The method of claim 62, wherein said estimate comprises a projected likely treatment outcome score.

64. The method of claim 63, wherein said treatment outcome score comprises a value selected from a set of values that form a treatment outcome scale, said treatment outcome scale including a likely success region, a likely failure region, and an intermediate region.

65. The method of claim 64, wherein said statistical model includes a discriminant function which includes a polynomial function.

66. The method of claim 65, wherein said statistical model includes a discriminant function which is derived using a similarity-metric least squares (SMILES) analysis of said data set.

67. The method of claim 66, wherein said disease is selected from the group consisting of AIDS, HBV, and HCV.

68. The method of claim 67, wherein said disease is HBV.

* * * * *